United States Patent [19]
Gold et al.

[11] Patent Number: 6,071,966
[45] Date of Patent: Jun. 6, 2000

[54] 1-AMINO-ALKYLCYCLOHEXANE NMDA RECEPTOR ANTAGONISTS

[75] Inventors: Markus Gold, Nauheim; Wojciech Danysz, Nidderau; Christopher Graham Raphael Parsons, Praunheim, all of Germany; Ivars Kalvinsh, Salaspils, Latvia; Valerjans Kauss; Aigars Jirgensons, both of Riga, Latvia

[73] Assignee: Merz + Co. GmbH & Co., Frankfurt am Main, Germany

[21] Appl. No.: 09/141,380

[22] Filed: Aug. 27, 1998

Related U.S. Application Data

[60] Continuation-in-part of application No. 09/048,575, Mar. 26, 1998, abandoned, which is a division of application No. 08/855,944, Jun. 30, 1997, abandoned.

[51] Int. Cl.[7] .................................................. A61K 33/00
[52] U.S. Cl. ............................................. 514/579; 514/659
[58] Field of Search ...................... 514/579, 659

[56] References Cited

U.S. PATENT DOCUMENTS

| | | | |
|---|---|---|---|
| 3,553,331 | 1/1971 | Paulshock | 424/325 |
| 3,652,769 | 3/1972 | Saaru | 424/325 |
| 5,032,616 | 7/1991 | Sauter et al. | 514/579 |
| 5,270,340 | 12/1993 | Kunisch et al. | 514/538 |

OTHER PUBLICATIONS

R.L. Frank, H.K. Hall (1950) J. Am. Chem. Soc. 72:1645–1648.
G.A. Hiegel, P. Burk. (1973) J. Org. Chem. 38:3637–3639.
N.F. Firrell, P.W. Hickmott. (1970) J. Chem. Soc. C:716–719.
G.H. Posner, L.L. Frye. (1984) Isr. J. Chem. 24:88–92.
G.L. Lemiere, T.A. van Osselaer, F.C. Anderweireldt. (1978) Bull. Soc. Chim. Belg. 87:771–782.
H.O. House, J.M. Wilkins. (1976) J. Org. Chem. 41:(25) 4031–4033.
A.R. Greenaway, W.B. Whalley. (1976) J. Chem. Soc. P.T. 1. :1385–1389.
S. Matsuzawa, Y. Horiguchi, E. Nakamura, I. Kuwajima. (1989) Tetrahedron 45:(2) 349–362.
H.O. House, W.F. Fischer, (1968) J. Org. Chem. 33:(3) 949–956.
Chiurdoglu, G., Maquestiau, A. (1954) Bull. Soc. Chim. Beig. 63: 357–378.
Zaidlewicz, M., Uzarewicz A., Zacharewicz, W. (1964) Roczniki Chem. 38: 591–597.
Crossley, A.W., Gilling, C. (1910) J. Chem. Soc. 2218.
Zaidlewicz, M., Uzarewicz, A. (1971) Roczniki Chem. 45: 1187–1194.
Lutz, E.T., van der Maas, J.H. (1982) Spectrochim. Acta, A. 38A: 283.
Lutz, E.T., van der Maas, J.H. (1981) Spectrochim. Acta, A. 37A: 129–134.
Ramalingam K., Balasubramanian, M., Baliah, V. (1972) Indian J. Chem. 10: 366–369.
Hamlin, K.E., Freifelder, M. (1953) J. Am. Chem. Soc. 75: 369–373.
Hassner, A., Fibinger, R., Andisik, D. (1984) J. Org. Chem. 49: 4237–4244.
W. Danysz, C.G. Parsons, I. Bresink, G. Quack (1995) Drug News Perspect. 8:261–277.
J.D. Leander, R.R. Lawson, P.L., Ornstein, D.M. Zimmerman (1988) Brain Res. 448:115–120.
C.G. Parsons, G. Quack, I. Bresink, L. Baran, E. Przegalinski, W. Kostowski, P. Krzascik, S. Hartmann, W. Danysz (1995). Neuropharmacology 34:1239–1258.
M.A. Rogawski (1993) Trends Pharmacol. Sci. 14:325–331.
Booher J. and Sensenbrenner M. (1972). Neurobiology 2:97–105.
Dichter, M. (1987) Brain Research 149:279.

*Primary Examiner*—Samuel Barts
*Attorney, Agent, or Firm*—The Firm of Gordon W. Hueschen

[57] ABSTRACT

Certain 1-aminoalkylcyclohexanes are systemically-active uncompetitive NMDA receptor antagonists having rapid blocking/unblocking kinetics and strong voltage-dependency and are therefore useful in the alleviation of conditions resulting from disturbances of glutamatergic transmission giving them a wide range of utility in the treatment of CNS disorders involving the same, as well as in non-NMDA indications, due to their immunomodulatory, antimalarial, anti-Borna virus, and anti-Hepatitis C activities and utilities. Pharmaceutical compositions thereof and a method-of-treating conditions which are alleviated by the employment of an NMDA receptor antagonist, as well as the aforementioned non-NMDA indications, and a method for the preparation of the active 1-aminoalkylcyclohexane compounds involved.

12 Claims, 2 Drawing Sheets

1-AMINO-ALKYLCYCLOHEXANE NMDA RECEPTOR ANTAGONISTS

The present application is a continuation-in-part of our prior-filed copending application Ser. No. 09/048,575 filed Mar. 26, 1998, now abandoned, which in turn is a division of our prior-filed application Ser. No. 08/885,944, filed Jun. 30, 1997, now abandoned.

BACKGROUND OF THE INVENTION

1. Field of the Invention

1-Amino-alkylcyclohexane compounds which are systemically-active as NMDA receptor antagonists, pharmaceutical compositions comprising the same, method of preparation thereof, and method of treating CNS disorders which involve disturbances of glutamatergic transmission therewith.

2. Prior Art

Antagonism of glutamate receptors of the N-methyl-D-aspartate (NMDA) type has a potentially wide range of therapeutic applications [19]. Functional inhibition of NMDA receptors can be achieved through actions at different recognition sites such as the primary transmitter site, strychnine-insensitive glycine site (glycine$_B$), polyamine site, and phencyclidine site located inside the cation channel. The NMDA receptor channel blockers act in an uncompetitive "use-dependent" manner, meaning that they usually only block the channel in the open state. This use-dependence has been interpreted by many to mean that stronger activation of the receptor should lead to a greater degree of antagonism. Such a mode of action has further been taken to imply that this class of antagonist may be particularly useful when overactivation of NMDA receptors can be expected, such as in epilepsy, ischaemia, and trauma. However, initial clinical experience with the selective, high affinity, strongly use-dependent uncompetitive NMDA receptor antagonist (+)-5-methyl-10,11-dihydro-5H-dibenzocyclohepten-5,10-imine maleate ((+)-MK-801) has been disappointing. Namely, therapeutic efficacy in epilepsy was poor while some psychotropic side effects were apparent at therapeutic doses. These observations, together with the fact that phencyclidine abusers experience similar psychotropic symptoms, has led to the conclusion that uncompetitive antagonism of NMDA receptors may not be a promising therapeutic approach.

However, the use of more elaborate electrophysiological methods indicates that there is no equality between different uncompetitive antagonists since factors such as the speed of receptor blockade (on-off kinetics) and the voltage-dependence of this effect may determine the pharmacodynamic features in vivo, i.e., therapeutic safety as well. Paradoxically, agents with low to moderate, rather than high, affinity may be desirable. Such findings -triggered a reconsideration of the concept of uncompetitive antagonism of NMDA receptors in drug development [19, 22]. At present, many such agents are at different stages of development, e.g., carvedilol, ADCI, ES 242S, remacemide, felbamate, and budipine. On the other hand, uncompetitive NMDA receptor antagonists, such as amantadine and memantine—which fulfill the above criteria—have been used clinically for several years in the treatment of Parkinson's disease and dementia respectively, and do indeed rarely produce side effects at the therapeutic doses used in their respective indications.

In view of the above mentioned evidence, we have developed a series of novel uncompetitive NMDA receptor antagonists based on the 1-aminoalkylcyclohexane structure. The present study was devoted to compare the NMDA receptor antagonistic properties of these 1-aminoalkylcyclohexane derivatives in receptor-binding assays, patch clamp experiments, excitotoxicity in vitro, three convulsion models, and two models of motor impairment. The substitutions of these 1-aminoalkylcyclohexanes are detailed in Table 6.

THE PRESENT INVENTION

It has now been found that certain 1-aminoalkylcyclohexanes have pronounced and unpredictable NMDA receptor antagonistic activity. Owing to the aforementioned property, the substances are suited for the treatment of a wide range of CNS disorders which involve disturbances of the glutamatergic transmission, preferably in the form of a pharmaceutical composition thereof wherein they are present together with one or more pharmaceutically-acceptable diluents, carriers, or excipients.

OBJECTS OF THE INVENTION

It is an object of the present invention to provide novel pharmaceutical compounds which are 1-aminoalkylcyclohexane NMDA receptor antagonists and pharmaceutical compositions thereof. It is a further object of the invention to provide a novel method of treating, eliminating, alleviating, palliating, or ameliorating undesirable CNS disorders which involve disturbances of glutamatergic transmission by the employment of such a compound of the invention or a pharmaceutical composition containing the same. An additional object of the invention is the provision of a process for producing the said 1-aminoalkylcyclohexane active principles. Yet additional objects will become apparent hereinafter, and still further objects will be apparent to one skilled in the art.

SUMMARY OF THE INVENTION

What we therefore believe to be comprised by our invention may be summarized inter alia in the following words:

A 1-aminoalkylcyclohexane compound selected from the group consisting of those of the formula

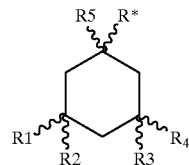

wherein R* is —(CH$_2$)$_n$—(CR$^6$R$^7$)$_m$—NR$^8$R$^9$ wherein n+m=0, 1, or 2 wherein R$^1$ through R$^7$ are independently selected from the group consisting of hydrogen and lower-alkyl (1–6C), at least R$^1$, R$^4$, and R$^5$ being lower-alkyl, and wherein R$^8$ and R$^9$ are independently selected from hydrogen and lower-alkyl (1–6C) or together represent lower-alkylene —(CH$_2$)$_x$— wherein x is 2 to 5, inclusive, and enantiomers, optical isomers, hydrates, and pharmaceutically-acceptable salts thereof;

such a compound wherein R$^1$ through R$^5$ are methyl;

such a compound wherein R$^1$ is ethyl;

such a compound wherein R$^2$ is ethyl;

such a compound wherein R$^3$ is ethyl;

such a compound wherein $R^4$ is ethyl;
such a compound wherein $R^5$ is ethyl;
such a compound wherein $R^5$ is propyl;
such a compound wherein $R^6$ or $R^7$ is methyl;
such a compound wherein $R^6$ or $R^7$ is ethyl; and
such a compound wherein the compound is selected from the group consisting of
1-amino-1,3,5-trimethylcyclohexane,
1-amino-1(trans),3(trans),5-trimethylcyclohexane,
1-amino-1(cis),3(cis),5-trimethylcyclohexane,
1-amino-1,3,3,5-tetramethylcyclohexane,
1-amino-1,3,3,5,5-pentamethylcyclohexane,
1-amino-1,3,5,5-tetramethyl-3-ethylcyclohexane,
1-amino-1,5,5-trimethyl-3,3-diethylcyclohexane,
1-amino-1,5,5-trimethyl-cis-3-ethylcyclohexane,
1-amino-(1S,5S)cis-3-ethyl-1,5,5-trimethylcyclohexane,
1-amino-1,5,5-trimethyl-trans-3-ethylcyclohexane,
1-amino-(1R,5S)trans-3-ethyl-1,5,5-trimethylcyclohexane,
1-amino-1-ethyl-3,3,5,5-tetramethylcyclohexane,
1-amino-1-propyl-3,3,5,5-tetramethylcyclohexane,
N-methyl-1-amino-1,3,3,5,5-pentamethylcyclohexane,
N-ethyl-1-amino-1,3,3,5,5-pentamethylcyclohexane, and
N-(1,3,3,5,5-pentamethylcyclohexyl) pyrrolidine, and hydrates, and pharmaceutically-acceptable salts of any of the foregoing.

Moreover, a method-of-treating a living animal for alleviation of a condition which is alleviated by an NMDA receptor antagonist, or for its immunomodulatory, antimalarial, anti-Borna virus, or anti-Hepatitis C effect, comprising the step of administering to the said living animal an amount of a 1-aminoalkylcyclohexane compound selected from the group consisting of those of the formula

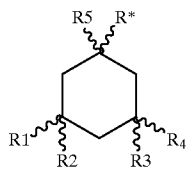

wherein R* is —$(CH_2)_n$—$(CR^6R^7)_m$—$NR^8R^9$
wherein n+m=0, 1, or 2
wherein $R^1$ through $R^7$ are independently selected from the group consisting of hydrogen and lower-alkyl (1–6C), wherein $R^8$ and $R^9$ are independently selected from hydrogen and lower-alkyl (1–6C) or together represent lower-alkylene —$(CH_2)_x$— wherein x is 2 to 5, inclusive, and optical isomers, enantiomers, hydrates, and pharmaceutically-acceptable salts thereof, which is effective for the said purpose;
such a method wherein $R^1$ through $R^5$ are methyl;
such a method wherein $R^1$ is ethyl;
such a method wherein $R^2$ is ethyl;
such a method wherein $R^3$ is ethyl;
such a method wherein $R^4$ is ethyl;
such a method wherein $R^5$ is ethyl;
such a method wherein $R^5$ is propyl;
such a method wherein $R^6$ or $R^7$ is methyl;
such a method wherein $R^6$ or $R^7$ is ethyl; and
such a method wherein the compound is selected from the group consisting of
1-amino-1,3,5-trimethylcyclohexane,
1-amino-1(trans),3(trans),5-trimethylcyclohexane,
1-amino-1(cis),3(cis),5-trimethylcyclohexane,
1-amino-1,3,3,5-tetramethylcyclohexane,
1-amino-1,3,3,5,5-pentamethylcyclohexane,
1-amino-1,3,5,5-tetramethyl-3-ethylcyclohexane,
1-amino-1,5,5-trimethyl-3,3-diethylcyclohexane,
1-amino-1,5,5-trimethyl-cis-3-ethylcyclohexane,
1-amino-(1S,5S)cis-3-ethyl-1,5,5-trimethylcyclohexane,
1-amino-1,5,5-trimethyl-trans-3-ethylcyclohexane,
1-amino-(1R,5S)trans-3-ethyl-1,5,5-trimethylcyclohexane,
1-amino-1-ethyl-3,3,5,5-tetramethylcyclohexane,
1-amino-1-propyl-3,3,5,5-tetramethylcyclohexane,
N-methyl-1-amino-1,3,3,5,5-pentamethylcyclohexane,
N-ethyl-1-amino-1,3,3,5,5-pentamethylcyclohexane, and
N-(1,3,3,5,5-pentamethylcyclohexyl) pyrrolidine, and hydrates and pharmaceutically-acceptable salts of any of the foregoing; and
such a method wherein the compound is administered in the form of a pharmaceutical composition thereof comprising the compound in combination with one or more pharmaceutically-acceptable diluents, excipients, or carriers.

Further, an NMDA-receptor antagonist pharmaceutical composition comprising an effective NMDA-receptor antagonistic amount, or an effective immunomodulatory, antimalarial, anti-Borna virus, or anti-Hepatitis C amount, of a 1-aminoalkylcyclohexane compound selected from the group consisting of those of the formula

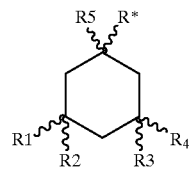

wherein R* is —$(CH_2)_n$—$(CR^6R^7)_m$—$NR^8R^9$
wherein n+m=0, 1, or 2
wherein $R^1$ through $R^7$ are independently selected from the group consisting of hydrogen and lower-alkyl (1–6C), at least $R^1$, $R^4$, and $R^5$ being lower-alkyl, and wherein $R^8$ and $R^9$ are independently selected from hydrogen and lower-alkyl (1–6C) or together represent lower-alkylene —$(CH_2)_x$— wherein x is 2 to 5, inclusive, and optical isomers, enantiomers, hydrates, and pharmaceutically-acceptable salts thereof, in combination with one or more pharmaceutically-acceptable diluents, excipients, or carriers;
such a pharmaceutical composition wherein $R^1$ through $R^5$ are methyl;
such a pharmaceutical composition wherein $R^1$ is ethyl;
such a pharmaceutical composition wherein $R^2$ is ethyl;
such a pharmaceutical composition wherein $R^3$ is ethyl;
such a pharmaceutical composition wherein $R^4$ is ethyl;
such a pharmaceutical composition wherein $R^5$ is ethyl;
such a pharmaceutical composition wherein $R^5$ is propyl;
such a pharmaceutical composition wherein $R^6$ or $R^7$ is methyl;
such a pharmaceutical composition wherein $R^6$ or $R^7$ is ethyl;
such a pharmaceutical composition wherein the compound is selected from the group consisting of
1-amino-1,3,5-trimethylcyclohexane,
1-amino-1(trans),3(trans),5-trimethylcyclohexane,
1-amino-1(cis),3(cis),5-trimethylcyclohexane, 1-amino-1,3,3,5-tetramethylcyclohexane,
1-amino-1,3,3,5,5-pentamethylcyclohexane,
1-amino-1,3,5,5-tetramethyl-3-ethylcyclohexane,
1-amino-1,5,5-trimethyl-3,3-diethylcyclohexane,
1-amino-1,5,5-trimethyl-cis-3-ethylcyclohexane,
1-amino-(1S,5S)cis-3-ethyl-1,5,5-trimethylcyclohexane,
1-amino-1,5,5-trimethyl-trans-3-ethylcyclohexane,
1-amino-(1R,5S)trans-3-ethyl-1,5,5-trimethylcyclohexane,
1-amino-1-ethyl-3,3,5,5-tetramethylcyclohexane,
1-amino-1-propyl-3,3,5,5-tetramethylcyclohexane,
N-methyl-1-amino-1,3,3,5,5-pentamethylcyclohexane,
N-ethyl-1-amino-1,3,3,5,5-pentamethylcyclohexane, and
N-(1,3,3,5,5-pentamethylcyclohexyl) pyrrolidine, and hydrates and pharmaceutically-acceptable salts of any of the foregoing.

DETAILED DESCRIPTION OF THE INVENTION

The following details and detailed Examples are given by way of illustration only, and are not to be construed as limiting.

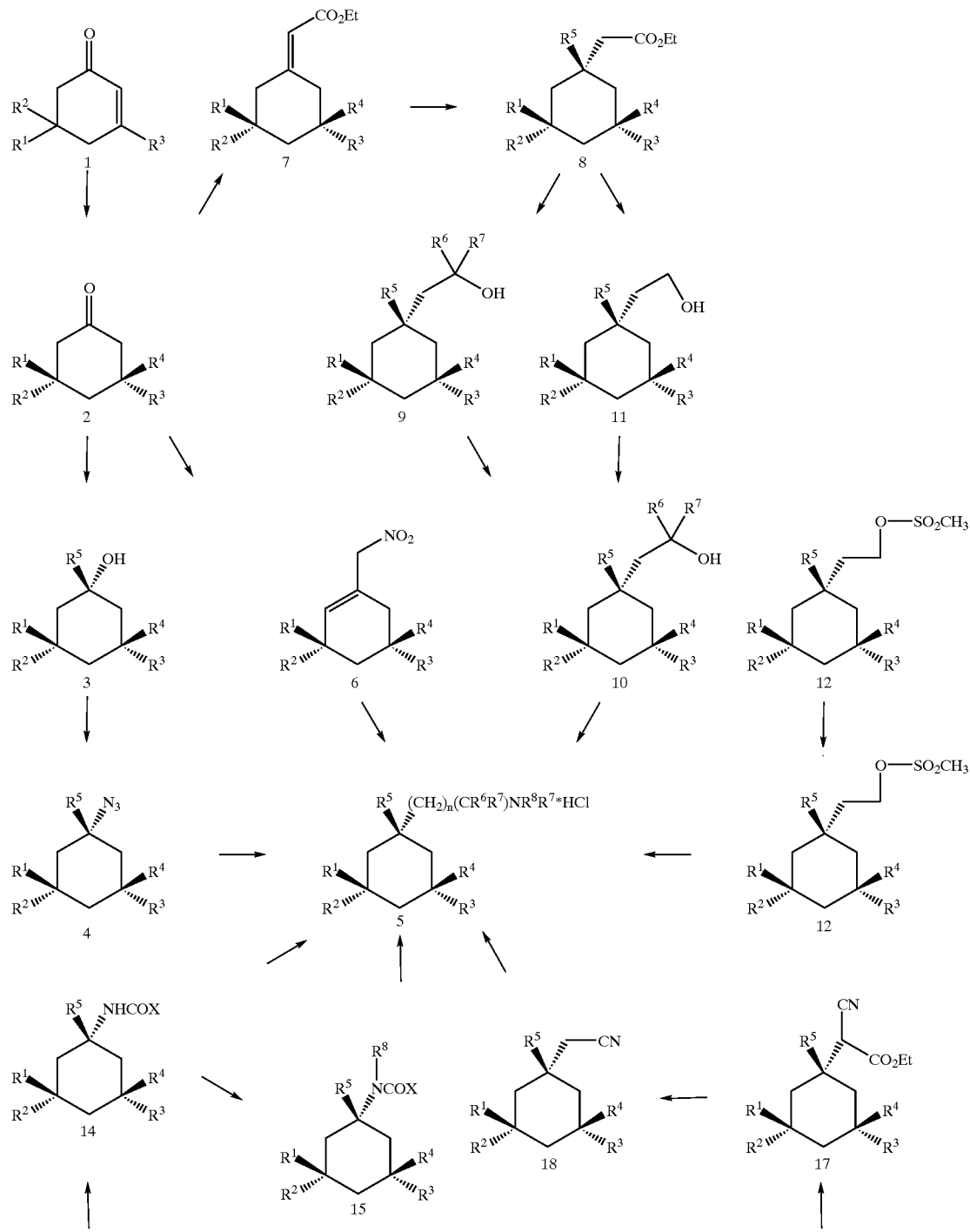

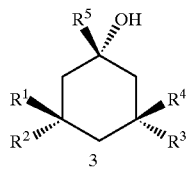
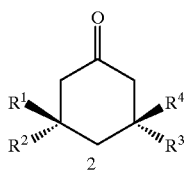
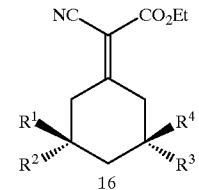

Preparation of 3-propyl-5,5-dimethyl-2-cyclohexene-1-one (1-7)

A solution of 3-ethoxy-5,5-dimethyl-2-cyclohexene-1-one [1] (5.04 g, 30 mmol) in ether was added dropwise to a stirred solution of propylmagnesium iodide prepared from 90 mg of magnesium and 90 mmol of 1-iodopropane in 60 ml of ether. After being stirred for 1 h at ambient temperature, the reaction mixture was treated with 5% $H_2SO_4$ solution. The organic phase was separated, washed with saline, dried over $MgSO_4$ and evaporated to give a crude oil which was separated on a silica gel column, eluting with hexane-ethyl acetate mixture. Cyclohexenone (1-7) was obtained as a colourless oil (2.0 g, 70%). $^1H$ NMR ($CDCl_3$, TMS) δ:0.92 (3H, t, J=7 Hz); 1.03 (6H,s); 1.3–1.75 (2H,m); 2.16 (2H, t, J=7 Hz); 2.17 (2H, d, J=1.5 Hz); 2.21 (2H,s) and 5.87 ppm (1H, t, J=1.5 Hz).

Such known cyclohexenones 1 were used to prepare compounds 2:

1-1 ($R^1=R^2=R^3=H$) [commerc. available],
1-2 ($R^3=Me$)* [commerc. available],
1-3 ($R^2=R^3=Me$) [commerce available],
1-4 ($R^1=R^2=Me$) [2],
1-5 ($R^1=R^2=R^3=Me$) [commerc. available],
1-6 ($R^1=R^2=Me, R^3=Et$) [3].

*$R''$=H, if omitted

Other starting materials 1 are prepared in the same or similar manner.

General procedure for preparation of cyclohexanones 2.

Anhydrous copper (1) chloride (7.5 mmol) was added to a cooled solution of alkylmagnesium iodide (15–18 mmol) in ether. The mixture was stirred in an inert atmosphere for 5 minutes and a solution of 2-cyclohexene-1-one 1 (10 mmol) in ether was added dropwise keeping the temperature below −5° C. After the addition of ketone was completed, the reaction mixture was stirred for 1 hour and carefully neutralized with saturated aqueous $NH_4Cl$ solution. Traditional workup for Grignard reactions gave crude material which was separated on a silica gel column, eluting with a petroleum ether-ethyl acetate mixture. The cyclohexanones 2 were obtained as oils.

Yields and $^1H$ NMR spectral data of compounds 2 are given in Table 1.

Such known cyclohexanones 2 were used to prepare compounds 3.

2-1 ($R^4=Me$)* [commerc. available],
2-2 ($R^4=Et$) [4],
2-3 ($R^4=Pr$) [5],
2-4 ($R^3=R^4=Me$) [6],
2-5 ($R^3=Me, R^4=Et$) [7],
2-6 ($R^3=Me, R^4=Pr$) [8],
2-7 ($R^1=R^4=Me$) [9],
2-8 ($R^2=R^3=R^4=Me$) [10],
2-9 ($R^2=R^3=Me, R^4=Et$) [11],
2-13 ($R^1=R^2=R^3=R^4=Me$) [commerc. available],
2-14 ($R^1=R^2=R^3=Me, R^4=Et$) [10],
2-15 ($R^1=R^2=R^3=Me, R^4=Pr$) [10].

*$R''$=H, if omitted.

Other intermediate cyclohexanones 2 are prepared in the same or a similar manner. Cyclohexanones 2 were used to prepare compounds 3:

General procedure for preparation of alkylcyclohexanols 3.

An etheral solution of alkylmagnesium iodide (3–4 equivalents) was added dropwise to a cooled solution of cyclohexanone 2 in ether. The mixture was stirred for 1 hour at ambient temperature and carefully destroyed with saturated aqueous ammonium chloride. Traditional workup for Grignard reactions gave mixtures of diastereomeric alcohols 3, which were separated on a silica gel column eluting with petroleum ether-ethyl acetate.

Yields and $^1H$ NMR spectral data of compounds 3 are given in Table 2.

Such known cyclohexanols 3 were used to prepare compounds 4:

3-1 (($R^3$)($R^4$)=$R^5$=Me)* [9], i.e., $R^3$ or $R^4$ and $R^5$ are Me.
3-4 ($R^3=R^4=Me, R^5=Me$) [12],
3-5 ($R^3=R =Me, R^4=Et$) [13],
3-7 ($R^1=R^4=R^5=Me$) [14],
3-8 ($R^1=R^3=R^4=R^5=Me$) [10],
3-13 ($R^1=R^2=R^3=R^4=R^5=Me$) [10],
3-14 ($R^1=R^2=R^3=R^4=Me, R^5=Et$) [15],

*$R''$=H, if omitted.

Other intermediate cyclohexenols 3 are prepared in the same or a similar manner.

General procedure for preparation of 1-alkyl-1-azidocyclohexanes 4.

The alcohol 3 was mixed with 1.7–2 N hydrazoic acid (10–13 equivalents) solution in chloroform, and cooled in an ice bath. A solution of $TiCl_4$ (1.2 equivalents) in chloroform was added dropwise while temperature was maintained below 5° C. The mixture was stirred at room temperature for 24 hours and passed down a column of alumina, eluting with chloroform. Evaporation of solvent provided diastereomeric azides 4 which were purified by flash chromatography on silica gel, eluting with light petroleum ether.

Yields and $^1H$ NMR spectral data of compounds 4 are given in Table 3.

Other intermediate 1-alkyl-1-azidocyclohexanes 4 are prepared in the same or a similar manner.

Preparation of 1-nitromethyl-3,3,5,5-tetramethylcyclohexene (6).

A solution of 3,3,5,5-tetramethylcyclohexanone (2-13) (1.54 g, 10 mmol) and ethylenediamine (60 mg) in nitromethane (45 ml) was refluxed in argon atmosphere for 25 h. Excess of nitromethane was then removed in vacuo and the residue was purified by flash chromatography on silica gel, eluting with hexane-ethyl acetate (6:1). 1.2 g (61%) of 6 was obtained as an oil.

$^1H$ NMR ($CDCl_3$, TMS) δ 0.96 and 1.03 (total 12H, both s, cyclohexane 3,5-$CH_3$); 1.34 (2H, s, 4-$CH_2$); 1.82 (2H, br s, 6-$CH_2$); 4.80 (2H, s, $CH_2NO_2$) and 5.64 ppm (1H, br s, C=C—H).

Preparation of ethyl 3,3,5,5-tetramethylcyclohexylideneacetate (7).

To a stirred solution of triethyl phosphonoacetate (49.32 g, 0.22 mol) in dry THF (180 ml) under argon NaH (8.8 g, 0.22 mol, 60% suspension in mineral oil) was added in small portions while cooling with ice water. Stirring was continued for 1 h at room temperature, then a solution of 3,3,5,5-tetramethylcyclohexanone (2-13) (30.85 g, 0.2 mol) was added over 10 min and the resulting mixture was refluxed for 22 h. It was then poured onto ice (400 g), the product was extracted with ether (4*150 ml) and the solution dried over $MgSO_4$. After concentration in vacuo an oily residue was distilled at 145° C. (11 mm) to give 36.8 g (86%) of 6 as an oil.

$^1$H NMR ($CDCl_3$, TMS) δ 0.96 and 0.98 (total 12H, both s, cyclohexane 3,5-$CH_3$); 1.27 (3H, t, $CH_3$-ethyl); 1.33 (2H, m, cyclohexane 4-$CH_2$); 1.95 and 2.65 (total 4H, both s, cyclohexane 2,6-$CH_2$); 4.14 (2H, q, $CH_2$-ethyl) and 5.69 ppm (1H, s, =C—H).

Preparation of ethyl 3,3,5,5-tetramethylcyclohexylacetate (8).

Ethyl 3,3,5,5-tetramethylcyclohexylideneacetate (7) (4.48 g, 20 mmol) in ethanol (100 ml) was hydrogenated over 10% Pd/C (0.22 g, 5 wt. %) at 10 atm for 18 h. Filtration through Celite™ and evaporation afforded 4.28 g (95%) of 8 as an oil.

$^1$H NMR ($CDCl_3$, TMS) δ 0.89 and 1.02 (total 12H, both s, —cyclohexane 3,5-$CH_3$); 1.26 (3H, t, J=7Hz, $CH_3$-ethyl); 0.6–1.55 (7H, m, ring protons); 2.13 (2H, m, 2-$CH_2$); and 4.12 ppm (2H, q, J=7Hz, $CH_2$-ethyl).

Preparation of 2-methyl-(3,3,5,5-tetramethylcyclohexyl)-propan-2-ol (9).

A solution of ethyl 3,3,5,5-tetramethylcyclohexylacetate (8) (2.26 g, 10 mmol) in ether (20 ml) was added dropwise to a 2 M methylmagnesium iodide solution in ether (20 ml) over 15 min, while cooling with ice water. The mixture was refluxed for 2 h, cooled and quenched with saturated aqueous $NH_4Cl$. After traditional workup the product was purified on silica gel column, eluting with a mixture of hexane-ethyl acetate (20:1) to give 1.7 g (80%) of 9 as an oil.

$^1$H NMR ($CDCl_3$, TMS) δ 0.86 and 1.00 (total 12H, both s, cyclohexane 3,5-$CH_3$); 1.23 (6H, s, α-$CH_3$); 1.36 (2H, d, J=5Hz, —$CH_2$—); 0.6–2.04 ppm (8H, m, ring protons and OH).

Preparation of 2-methyl-(3,3,5,5-tetramethylcyclohexyl)-propyl-2-azide (10).

Boron trifluoride etherate (0.77 g, 0.69 ml, 5.44 mmol) was added dropwise to a stirred solution of 2-methyl-(3,3,5,5-tetramethylcyclohexyl)-propan-2-ol (9) (0.96 g, 4.53 mmol) and trimethylsilyl azide (0.63 g, 0.72 ml, 5.44 mmol) in benzene (10 ml). After being stirred for 24 h at room temperature the mixture was poured into water (20 ml). The organic phase was separated and washed with saturated aqueous $NaHCO_3$ (10 ml) and saline (10 ml). The solution was dried over $MgSO_4$, filtered and concentrated. The crude product was purified on silica gel column, eluting with hexane to give 0.56 g (52%) of 10 as an oil.

$^1$H NMR ($CDCl_3$, TMS) δ: 0.87 and 1.01 (total 12H, both s, cyclohexane 3,5-$CH_3$); 1.27 (6H, s. α-$CH_3$); 1.36 (2H, d, J=5Hz, —$CH_2$—); 0.6–1.85 ppm (7H, m, ring protons).

Preparation of 2-(3,3,5,5-tetramethylcyclohexyl)-ethanol (11).

A solution of ethyl 3,3,5,5-tetramethylcyclohexylacetate 8 (1.8 g, 8.0 mmol) in ether (30 ml) was added dropwise to a stirred suspension of lithium aluminum hydride (0.9 g, 24.0 mmol) in ether (30 ml), which was cooled in an ice bath. The reaction mixture was refluxed for 3 h, cooled and residual lithium aluminum hydride was destroyed with water. The aqueous layer was separated and twice extracted with ether. The combined ether phases were washed with saline, dried over $MgSO_4$, filtered and evaporated. The crude product was purified by flash chromatography on silica gel, eluting with hexane-ethyl acetate mixture (4:1) to give 1.2 g (79%) of 11 as an oil.

$^1$H NMR ($CDCl_3$, TMS) δ: 0.89 and 1.00 (total 12H, both s, cyclohexane 3,5-$CH_3$); 1.44 (2H, q, J=7 Hz, 2-$CH_2$); 0.55–1.95 (8H, m, ring protons and OH) and 3.70 ppm (2H, t, J=7 Hz, $CH_2O$).

Preparation of 2-(3,3,5,5-tetramethylcyclohexyl)-ethyl methanesulfonate(12).

A solution of methanesulfonyl chloride (1.03 g, 0.7 ml, 9.0 mmol) in dry benzene (20 ml) was added to a stirred solution of 2-(3,3,5,5-tetramethylcyclohexyl)-ethanol (11) (1.1 g, 6.0 mmol) and triethylamine (1.2 g, 1.7 ml, 12 mmol) in benzene (40 ml), while cooling in an ice bath. The reaction mixture was stirred at room temperature for 3 h, then filtered through a short silica gel column, eluting with benzene. Evaporation of solvent gave 1.48 g (94%) of 12 as an oil.

$^1$H NMR ($CDCl_3$, TMS) δ: 0.88 and 0.98 (total 12H, both s, cyclohexane 3,5-$CH_3$); 1.62 (2H, q, J=7 Hz, 2-$CH_2$); 0.65–2.0 (7H, m, ring protons) 3.0 (3H, s, $CH_3$—$SO_2$) and 4.29 ppm (2H, t, J=7 Hz, $CH_2O$).

Preparation of 2-(3,3,5,5-tetramethylcyclohexyl)-ethylazide (13).

The mixture of sodium azide (2.27 g, 34.2 mmol), 2-(3,3,5,5-tetramethylcyclohexyl)-ethyl methanesulfonate-(12) (1.46 g, 5.57 mmol) and dimethyl sulfoxide (20 ml) was stirred at room Temperature for 48 h, diluted with water (50 ml) and extracted with ether (3*30 ml). The organic phase was washed with saline (30 ml), dried over $MgSO_4$, filtered and evaporated. The crude product was purified by flash chromatography on silica gel, eluting with hexane to give 0.93 g (80%) of (13) as an oil.

$^1$H NMR ($CDCl_3$, TMS) δ: 0.87 and 0.99 (total 12H, both s, cyclohexane 3,5-$CH_3$); 1.47 (2H, q, J=7 Hz, 2-$CH_2$); 0.55–1.9 (7H, m, ring protons) and 3.31 ppm (2H, t, J=7 Hz, $CH_2N_3$).

Preparation of N-formyl-1,3,3,5,5-pentamethylcyclohexanamine (14-1).

To a vigorously stirred solution of 1,3,3,5,5-pentamethylcyclohexanol (3-13) (2.7 g, 15.6 mmol) and trimethylsilyl cyanide (2.36 g, 23.8 mmol) in acetic acid (2.5 ml) under argon 98% sulfuric acid (4.66 g, 47.6 mmol) was added, keeping temperature below −5° C. The mixture was stirred at room temperature for 22 h, then it was poured onto ice (100 g), neutralised with 50% NaOH solution to pH ~7 and extracted with ether (3*30 ml). The combined ether phases were washed with saline (50 ml), then dried over $MgSO_4$ and evaporated. A slightly yellow crystalline residue was treated with small amount of acetonitrile and filtered off to give 2.5 g (80%) of 14-1 as a white crystals, m.p. 104–106° C. $^1$H NMR ($CDCl_3$, TMS) δ: 0.91 and 0.93 (total 6H, both s, 3,5-$CH_{3eq}$); 1.08 (2H, m, 2,6-$CH_{eq}$); 1.13 and 1.15 (total 6H, both s, 3,5-$CH_{3ax}$); 1.25 (2H, m, 4-$CH_2$); 1.32 and 1.38 (total 3H, both s, 1-$CH_3$); 1.70 and 2.12 (total 2H, both d, 14.7 Hz, 2,6-$CH_{ax}$); 5.30 and 5.60 (total 1H, both br s, NH); 8.05 and 8.30 ppm (total 1H, both d, 2.0 and 12.7 Hz, resp., HCO).

Preparation of N-acetyl-1,3,3,5,5-pentamethylcyclohexanamine (14-2).

To a vigorously stirred solution of 1,3,3,5,5-pentamethylcyclohexanol (3-13) (3.0 g, 17.65 mmol) in acetonitrile (20 ml) fuming $HNO_3$ (6ml) was added dropwise, keeping temperature below 45° C. The resulting mixture was stirred at −50° C. for 6 h, then it was cooled, poured into water (30 ml) ana neutralised with aqueous $NH_3$. Aqueous phase was extracted with ether (3*30 ml). The combined ether phases were washed with saline (30 ml), then dried over $MgSO_4$, filtered and evaporated. The crude product was crystallised from cold acetonitrile to give 223 g (60%) of 14-2 as a white crystals, m.p. 110° C.

$^1$H NMR ($CDCl_3$, TMS) δ: 0.90 and 1.12 (total 12H, both s, 3,5-$CH_3$); 1.33 (3H, s, 1-$CH_3$); 1.88 (3H, s, $CH_3C$=O); 0.75–2.25 (6H, m, ring protons) and 5.3 ppm (1H, br s, NH). Preparation of N-methoxycarbonyl-N,1,3,3,5,5-hexamethylcyclohexanamine (15).

Methyl chloroformate (0.97 g, 0.8 ml, 10.3 mmol) was added in one portion to a suspension of N,1,3,3,5,5-hexamethylcyclohexanamine hydrochloride (5-20) (1.13 g, 5.13 mmol) and $Na_2CO_3$ (1.63 g, 15.4 mmol) in THF (30 ml). The resulting mixture was stirred at room temperature for 6 h, and then it was diluted with water (50 ml) and extracted with ether (3*30ml). The combined organic phases were washed with 10% $K_2SO_4$, saline, dried over $MgSO_4$, filtered and evaporated. The crude product was purified by flash chromatography, eluting with hexane-ethyl acetate mixture (6:1) to give 0.90 g (78%) of (15) as an oil.

1H NMR ($CDCl_3$, TMS) δ: 0.93 and 1.07 (total 12H, both s, 3,5-$CH_3$); 1.23 (3H, s, 1-$CH_3$); 1.0–1.4 (4H, m, 4-$CH_2$ and 2,6-$CH_{eq}$); 2.56 (2H, d, J=14 Hz, 2,6-$CH_{ax}$); 2.87 (3H, s, $CH_3N$) and 3.64 ppm (3H, s, $CH_3$0).
Preparation of ethyl (3,3,5,5-tetramethylcyclohexylidene) cyanoacetate (16).

The mixture of 3,3,5,5-tetramethylcyclohexanone (2-13) (2.64g, 17 mmol), ethyl cyanoacetate (1.93, 17 mmol), acetic acid (0.2 ml) and ammonium acetate (0.2 g) in benzene (6.4 ml) was refluxed with a Dean-Stark aparatus for 10 h. To this benzene (30 ml) and saline (30 ml) was added, organic layer separated, dried over $Na_2SO_4$, filtered and evaporated. The crude product was purified by flash chromatography, eluting with hexane to give 2.0 g (50%) of (16) as an oil.

$^1$H NMR ($CDCl_3$, TMS) δ: 1.01 (6H, s, 3,5-$CH_{3eq}$); 1.05 (6H, s, 3,5-$CH_{3}$ax); 1.34 (3H, t, J=7Hz, ethyl-$CH_3$); 1.42 (2H, s, 4-CH?); 2.46 and 2.79 (total 4H, both s, 2,6-$CH_2$) and 4.29 ppm (2H, q, J=7 Hz, $CH_2$O).
Preparation of ethyl (1,3,3,5,5-pentamethylcyclohexyl) cyanoacetate (17).

Anhydrous copper (I) chloride (0.8 g, 8 mmol) was added to a cooled solution of alkylmagnesium iodide (prepared from magnesium (0.46 g, 19.2 mmol) and iodomethane (2.84 g, 20 mmol)) in ether (12 ml). The mixture was stirred in an inert atmosphere for 5 min and a solution of ethyl (3,3,5,5-tetramethylcyclohexylidene)cyanoacetate (16) (2 g, 8 mmol) in ether (10 ml), was added dropwise keeping the temperature below −1 5 C. After the addition of ketone was completed, the reaction mixture was stirred for 3 h and carefully neutralised with saturated aqueous $NH_4Cl$ solution. Traditional workup for Grignard reactions gave crude material which was separated on a silica gel column, eluting with a petroleum ether-ethyl acetate mixture (20:1) to give 1.0 g (47%) of 17 as an oil.

$^1$H NMR ($CDCl_3$, TMS) δ: 0.98 (9H, s, 3,5-$CH_{3eq}$ and 1-$CH_3$); 1.06 (6H, s, 3,5-$CH_{3ax}$); 1.31 (3H, t, J=7 Hz, ethyl-$CH_3$); 1.2–1.5 (6H, m, ring protons); 3.41 (1H, s, α-CH) and 4.25 ppm (2H, q, J=7Hz, $CH_2$O).
Preparation of 1-cyanomethyl-1,3,3,5,5-pentamethylcyclohexane (18).

The mixture of ethyl (1,3,3,5,5-pentamethylcyclohexyl) cyanoacetate (17) (1g, 3,7 mmol), LiCl (0.05 g) and water (0.15 ml) in DMSO (2.5ml) was heated at 150–160° C. for 4 h. Solution was poured into water (70 ml) and extracted with ether (4*20 ml). Ether was washed with saline (2*50 ml), dried over $Na_2SO_4$, filtered and evaporated. Crude product was purified on silica gel column, eluting with a petroleum ether-ethyl acetate mixture (20:1) to give 0.66 g (94%) of 18 as an oil.

$^1$H NMR ($CDCl_3$, TMS) δ: 0.98 (9H, s, 3,5-$CH_{3eq}$ and 1-$CH_3$); 1.02 (6H, s, 3,5-$CH_{3ax}$); 1.21 (3H, s, ring protons); 1.31 (3H, s, ring protons) and 2.31 ppm (2H, s, $CH_2CN$). IR (neat) $v_{CN}$=2242 $cm^{-1}$.
General procedure for preparation of alkylcyclohexanamine hydrochlorides 5-1–5-25.

A solution of 4, 10 or 13–15, 18 in ether was added dropwise to a stirred suspension of lithium aluminum hydride (4 equivalents) in ether, which was cooled in an ice bath. The reaction mixture was stirred at room temperature in the case of 4, 10, 13 or refluxed in the case of 14, 15, 18 till complete conversion of starting material (TLC control). Residual lithium aluminum hydride was destroyed with water, the aqueous layer separated and twice extracted with ether. The combined ether phases were washed with saline, dried over NaOH, filtered and evaporated. The amine obtained was treated with HCl without characterization. The amine hydrochloride was prepared either by passing of HCl gas through the amine solution in hexane or by addition of a 1 N HCl solution in ether to the amine solution. In both cases the solvent was removed after HCl addition, the residue treated with hexane or acetonitrile and the crystalline product filtered off to give 5-1–5-25 with excellent purity.

The physical properties and yields of compounds 5-1–5-25 are given in Table 4.

$^1$H NMR spectral data of compounds 5-1–5-25 are given in Table 5.

Additional 1-aminoalkylcyclohexanes and their hydrochlorides are prepared in the same or a similar manner. The hydrochlorides can be converted to the free base or other acid addition salts as disclosed under "ACID ADDITION SALTS".
Preparation of 3,3,5,5-tetramethylcyclohexylmethylamine hydrochloride (5-26).

A solution of 1-nitromethyl-3,3,5,5-tetramethylcyclohexene (6) (1.1 g, 5.63 mmol) in a mixture of ethanol (140 ml) and chloroform (2.8 ml) was hydrogenated over 10% Pd/C (280 mg) at 5 atm for 20 h, filtered and evaporated. The crude product was treated with ether, filtered and washed with ether to give 0.57 g (50%) of amine 5-26.

The physical properties and yield of compound 5-26 are given in Table 4.

$^1$H NMR spectral data of compound 5-26 are given in Table 5.

Amine 5-27 was prepared according to the known procedure [16].

Amine 5-28 [17] was prepared according to the general procedure from corresponding azide [18]. All physical properties were in good agreement with data described [17].

The purity of all compounds prepared was checked by GC (MN-OV-1, 25m*0.53m, $d_f$=1.0 μm, 50–270° C. (10° C./min)).

ACID ADDITION SALTS

As acids suitable for the formation of acid addition salts according to conventional procedure, there may be mentioned from the mineral series the following acids: hydrochloric, hydrobromic, methanesulfonic, isothionic, sulfuric, phosphoric, and sulfamic acids and, from the organic series: acetic, propionic, maleic, fumaric, tartaric, citric, oxalic, and benzoic acids, to name a few. Preferred acids are hydrochloric, citric, and maleic. Other pharmaceutically-acceptable acid addition salts may be prepared, if desired, and one acid addition salt may be converted into another by neutralizing one salt, for example, the hydrochloride, resulting in the free base, and then reacidifying with a different selected mineral or organic acid, to prepare another pharmaceutically-acceptable acid addition salt, as is conventional in the art.

TABLE 1

Cyclohexanones 2

| Compd. | $R^1$ | $R^2$ | $R^3$ | $R^4$ | Yield (%) | $^1$H—NMR (CDCl$_3$, TMS) δ ppm |
|---|---|---|---|---|---|---|
| 2-10 | Me | | Me | Pr | 81.5 | 0.86(3H, t, 6Hz); 0.98(3H, s); 1.01(3H, d, 5Hz); 1.05–1.35(4H, m); 1.55–2.05(4H, m); 2.11(2H, s); 2.34(1H, m) |
| 2-11 | Me | Me | | Et | 54 | 0.88(3H, s); 0.90(3H, t, 7Hz); 1.06(3H, s); 1.15–1.45(2H, m); 2.13(2H, s); 1.45–2.45(5H, m) |
| 2-12 | Me | Me | | Pr | 74 | 0.87(6H, m); 1.15(3H, s); 1.15–1.45(4H, m); 2.13(2H, s); 1.45–2.45(5H, m) |
| 2-16 | Me | Me | Et | Et | 83.5 | 0.78(6H, t, 7Hz); 1.04(6H, s); 1.37(2H, q, 7Hz); 1.52(2H, s); 2.16(4H, s) |
| 2-17 | Me | Me | Pr | Pr | 79 | 0.87(6H, m); 1.03(6H, s); 1.25(8H, m); 1.53(2H, s); 2.16(4H, s) |

TABLE 2

1-Alkylcyclohexanols 3

| Compd. | $R^1$ | $R^2$ | $R^3$ | $R^4$ | $R^5$ | Yield (%) | $^1$H—NMR(CDCl$_3$, TMS)δ ppm |
|---|---|---|---|---|---|---|---|
| 3-2a | | | | Et | Me | 93 | 0.84(3H, t, 7Hz); 1.17(3H, s); 1.0–1.85(12H, m) |
| 3-2b | | | Et | | Me | | 0.87(3H, t. 7Hz); 1.21(3H, s); 1.0–1.85(12H, m) |
| 3-3a | | | | Pr | Me | 93 | 0.86(3H, t, 7Hz); 1.18(3H, s); 1.0–1.9(14H, m) |
| 3-3b | | | Pr | | Me | | 0.86(3H, t, 7Hz); 1.19(3H, s); 1.0–1.85(14H, m) |
| 3-6a | | | Me | Pr | Me | 88 | 0.83(3H, s,); 0.86(3H, m); 1.19(3H, s); 1.0–1.85(13H, m) |
| 3-6b | | | Pr | Me | Me | | 0.86(3H, t, 6.5Hz); 1.04(3H. s); 1.17(3H, s); 0.95–1.95(13H, m) |
| 3-9 | Me | | Et | Me | Me | 94 | 0.80(3H, s); 0.81(3H, t, 7Hz); 0.86(3H, d, 6.5Hz); 1.17(3H, s);0.9–2.0(10H, m) |
| 3-10 | Me | | Pr | Me | Me | 86 | 0.81(6H, m); 0.86(3H, d, 6.5Hz); 1.17(3H, s); 0.9–2.0(12H, m) |
| 3-11 | Me | Me | | Et | Me | 84 | 0.87(6H, m); 1.08(3H, s); 1.18(3H, s); 0.95–1.95(10H, m) |
| 3-12 | Me | Me | | Pr | Me | 88 | 0.88(6H, m); 1.09(3H, s); 1.18(3H, s); 0.9–1.95(12H, m) |
| 3-15 | Me | Me | Me | Me | Pr | 85 | 0.89(9H, m); 1.21(6H, s); 0.95–1.7(11H, m) |
| 3-16 | Me | Me | Me(Et) | Et(Me) | Me | 89 | 0.81(3H, t, 7Hz); 0.89, 1.17 and 1.21(total 12H, all s); 0.9–1.35(5H, m); 1.35–2.0(4H, m) |
| 3-17 | Me | Me | Me(Pr) | Pr(Me) | Me | 88 | 0.84(3H, m); 0.88 and 1.19(total 12H, both s); 0.9–1.35(7H, m); 1.35–2.0(4H, m) |
| 3-18 | Me | Me | Et | Et | Me | 87 | 0.78(6H, t, 7Hz); 0.89(3H, s); 1.19(6H, s); 0.95–1.3(7H, m); 1.3–2.05(4H, m) |
| 3-19 | Me | Me | Pr | Pr | Me | 90 | 0.86(6H, t, 6.5); 0.88(3H, s); 1.18(6H, s); 0.9–1.3(11H, m); 1.3–2.05(4H, m) |

TABLE 3

1-Alkyl-1-azidocyclohexanes 4

| Compound | $R^1$ | $R^2$ | $R^3$ | $R^4$ | $R^5$ | Yield (%) | $^1$H—NMR(CDCl$_3$, TMS)δ ppm |
|---|---|---|---|---|---|---|---|
| 4-1a | | | | Me | Me | 31 | 0.89(3H, d, 6.5Hz); 1.31(3H; s); 0.95–2.0(9H, m) |
| 4-1b | | | Me | | Me | 6 | 0.92(3H, d, 6.5Hz); 1.28(3H, s); 1.0–2.0(9H, m) |
| 4-2a | | | | Et | Me | 26 | 0.88(3H, t, 7Hz); 1.29(3H. s); 0.95–2.0(11H, m) |
| 4-2b | | | Et | | Me | 4 | 0.88(3H, t, 6.5Hz); 1.27(3H, s); 1.0–2.0(11H, m) |
| 4-3a | | | | Pr | Me | 24 | 0.88(3H, t, 6.5Hz); 1.29(3H, s); 1.0–2.0(13H, m) |
| 4-3b | | | Pr | | Me | 11 | 0.88(3H, t, 6.5Hz); 1.27(3H, s); 1.0–2.0(13H, m) |
| 4-4 | | | Me | Me | Me | 60 | 0.90(3H, s); 1.08(3H, s); 1.27(3H, s); 1.0–1.95(8H, m) |
| 4-5 | | | Me(Et) | Et(Me) | Me | 60 | 0.82 and 1.04(total 3H, s); 0.82(3H, t, 7Hz); 1.28 and 1.29(total 3H, s); 9.9–2.0(10H, m) |
| 4-6 | | | Me(Pr) | Pr(Me) | Me | 66 | 0.85 and 1.07(total 3H, s); 0.87 and 0.90(total 3H, t, 6,5Hz); 1.29(3H, s); 1.0–1.95(12H, m) |
| 4-7 | Me(H) | H(Me) | H(Me) | Me(H) | Me | 31 | 0.87(6H, d, 6Hz); 1.27 and 1.29(total 3H, s); 0.95–2.15(8H, m) |
| 4-8a | Me | | Me | Me | Me | 42 | 0.86(3H, d, 6Hz); 0.89(3H, s); 1.09(3H, s); 1.27(3H, s); 9.95–1.9(7H, m) |
| 4-8b | | Me | Me | Me | Me | 12 | 0.92(3H, d, 6.5Hz); 0.94(3H, s); 0.97(3H, s); 1.36(3H, s); 0.95–2.0(7H, m) |
| 4-9a | Me | | Et | Me | Me | 47 | 0.81(6H, s and m); 0.86(3H, d, 6Hz); 1.27(3H, s); 0.95–1.95(9H, m) |
| 4-9b | | Me | Me | Et | Me | 12 | 0.81(3H, t, 7Hz); 0.87(3H, s); 0.91(3H, d, 6Hz); 1.34(3H s) 1.95(9H m) |
| 4-10a | Me | | Pr | Me | Me | 44 | 0.81(3H, s); 0.84(3H, d, 6Hz); 0.87(3H, m); 1.27(3H, s); 1.0–2.0(11H, m) |
| 4-10b | | Me | Me | Pr | Me | 9 | 0.88(6H, s and m); 0.91(3H, d, 6Hz); 1.34(3H, s); 1.0–1.95(11H, m) |
| 4-11a | Me | Me | | Et | Me | 45 | 0.91(3H, t, 7Hz); 0.92(3H, s); 1.12(3H, s); 1.31(3H, s), 1.0–1.9(9H, m) |
| 4-11b | Me | Me | Et | | Me | 12 | 0.92(3H, t, 7Hz); 0.97 and 0.99(total 6H, s); 1.37(3H, s), 1.0–1.9(9H, m) |
| 4-12a | Me | Me | | Pr | Me | 54 | 0.90(6H, s and m); 1.10(3H, s); 1.28(3H, s); 0.95–1.9(11H, m) |
| 1-12b | Me | Me | Pr | | Me | 7 | 0.89(3H, t, 7Hz); 0.95(3H, s); 0.98(3H, s); 1.37(3H, s); 1.0–1.9(11H, m) |

TABLE 3-continued

1-Alkyl-1-azidocyclohexanes 4

| Compound | $R^1$ | $R^2$ | $R^3$ | $R^4$ | $R^5$ | Yield (%) | $^1$H—NMR(CDCl$_3$, TMS)δ ppm |
|---|---|---|---|---|---|---|---|
| 4-13 | Me | Me | Me | Me | Me | 67 | 0.89(6H, s); 1.18(6H, s); 1.29(3H, s); 0.95–1.9(6H, m) |
| 4-14 | Me | Me | Me | Me | Et | 39 | 0.89(6H, s); 0.96(3H, t, 7Hz); 1.19(6H, s); 1.0–1.9(8H, m) |
| 4-15 | Me | Me | Me | Me | Pr | 65 | 0.89(6H, s); 0.93(3H, m); 1.16(6H, s); 1.0–1.8(10H, m) |
| 4-16 | Me | Me | Me(Et) | Et(Me) | Me | 77 | 0.82(3H, m); 0.89, 1.14 and 1.18(total 9H, s); 1.26 and 1.29(total 3H, s); 0.95–1.9(8H, m) |
| 4-17 | Me | Me | Me(Pr) | Pr(Me) | Me | 71 | 0.86; 0.88(total 3H, t, 6.5Hz); 0.90, 1.17; 1.19(total 9H, s); 1.28; 1.32(total 3H); 0.95–1.9(10H, m) |
| 4-18 | Me | Me | Et | Et | Me | 66 | 0.78(6H, t, 7Hz); 0.90(3H, s); 1.18(3H, s); 1.31(3H, s); 0.95–1.95(10H, m) |
| 4-19 | Me | Me | Pr | Pr | Me | 61 | 0.89(9H, s and m); 1.17(3H, s); 1.27(3H, s); 0.95–1.95(14H, m) |

TABLE 4

Amino-cyclohexane derivatives 5

| Mrz2/ | Comp | Formula | M.W. | Calculated(%) C | H | N | Found(%) C | H | N | m.p. (° C.) | Yield (%) |
|---|---|---|---|---|---|---|---|---|---|---|---|
| 625 | 5-1a | C$_8$H$_{17}$N*HCl | 163.72 | 58.7 | 10.5 | 8.6 | 58.7 | 10.5 | 8.6 | >250 | 63 |
| 631 | 5-1b | C$_8$H$_{17}$N*HCl | 163.72 | 58.7 | 10.5 | 8.6 | 58.7 | 10.5 | 8.6 | 200–202 | 48 |
| 629 | 5-2a | C$_9$H$_{19}$N*HCl | 177.75 | 60.8 | 10.8 | 7.9 | 60.8 | 10.8 | 7.9 | >250 | 66 |
| 630 | 5-2b | C$_9$H$_{19}$N*HCl | 177.75 | 60.8 | 10.8 | 7.9 | 60.8 | 10.8 | 7.9 | 179–181 | 43 |
| 627 | 5-3a | C$_{10}$H$_{21}$N*HCl | 191.78 | 62.6 | 11.1 | 7.3 | 62.6 | 11.1 | 7.3 | >250 | 80 |
| 626 | 5-3b | C$_{10}$H$_{21}$N*HCl | 191.78 | 62.6 | 11.1 | 7.3 | 62.6 | 11.1 | 7.3 | 181–182 | 81 |
| 621 | 5-4 | C$_9$H$_{19}$N*HCl | 177.75 | 60.8 | 10.8 | 7.9 | 60.8 | 10.8 | 7.9 | 230–231 | 73 |
| 620 | 5-5 | C$_{10}$H$_{21}$N*HCl | 191.78 | 62.6 | 11.1 | 7.3 | 62.6 | 11.1 | 7.3 | 168–170 | 71 |
| 617 | 5-6 | C$_{11}$H$_{23}$N*HCl | 205.81 | 64.2 | 11.3 | 6.8 | 64.2 | 11.3 | 6.8 | 106–108 | 68 |
| 616 | 5-7 | C$_9$H$_{19}$N*HCl | 177.75 | 60.8 | 10.8 | 7.9 | 60.8 | 10.8 | 7.9 | 280–282 | 50 |
| 607 | 5-8a | C$_{10}$H$_{21}$N*HCl | 191.78 | 62.6 | 11.1 | 7.3 | 62.6 | 11.1 | 7.3 | >240 | 74 |
| 622 | 5-9a | C$_{11}$H$_{23}$N*HCl | 205.81 | 64.2 | 11.3 | 6.8 | 64.2 | 11.3 | 6.8 | 250–253 | 68 |
| 624 | 5-9b | C$_{11}$H$_{23}$N*HCl | 205.81 | 64.2 | 11.3 | 6.8 | 64.2 | 11.3 | 6.8 | 228–231 | 60 |
| 618 | 5-10a | C$_{12}$H$_{25}$N*HCl | 219.84 | 65.6 | 11.9 | 6.4 | 65.6 | 11.5 | 6.4 | 167–168 | 57 |
| 619 | 5-10b | C$_{12}$H$_{25}$N*HCl | 219.84 | 65.6 | 11.9 | 6.4 | 65.6 | 11.5 | 6.4 | 237–238 | 36 |
| 633 | 5-11a | C$_{11}$H$_{23}$N*HCl | 205.81 | 64.2 | 11.3 | 6.8 | 64.2 | 11.3 | 6.8 | 255–257 | 69 |
| 632 | 5-11b | C$_{11}$H$_{23}$N*HCl | 205.81 | 64.2 | 11.3 | 6.8 | 64.2 | 11.3 | 6.8 | 216–218 | 44 |
| 635 | 5-12a | C$_{12}$H$_{25}$N*HCl | 219.84 | 65.6 | 11.9 | 6.4 | 65.6 | 11.5 | 6.4 | 218–221 | 83 |
| 634 | 5-12b | C$_{12}$H$_{25}$N*HCl | 219.84 | 65.6 | 11.9 | 6.4 | 65.6 | 11.5 | 6.4 | 200–203 | 44 |
| 579 | 5-13 | C$_{11}$H$_{23}$N*HCl | 205.81 | 64.2 | 11.3 | 6.8 | 64.2 | 11.3 | 6.8 | 235–237 | 82 |
| 600 | 5-14 | C$_{12}$H$_{25}$N*HCl*H$_2$O | 237.86 | 60.6 | 10.6 | 5.9 | 60.6 | 10.6 | 5.9 | 215–218 | 74 |
| 601 | 5-15 | C$_{13}$H$_{27}$N*HCl | 233.87 | 66.8 | 11.7 | 6.0 | 66.8 | 11.7 | 6.0 | >280 | 88 |
| 615 | 5-16 | C$_{12}$H$_{25}$N*HCl | 219.84 | 65.6 | 11.9 | 6.4 | 65.6 | 11.5 | 6.4 | 162–163 | 65 |
| 614 | 5-17 | C$_{13}$H$_{27}$N*HCl*0.5H$_2$ | 242.84 | 64.3 | 12.0 | 5.8 | 63.8 | 12.0 | 5.6 | 106–107 | 54 |
| 623 | 5-18 | C$_{13}$H$_{27}$N*HCl*H$_2$O | 251.89 | 62.0 | 10.8 | 5.6 | 62.0 | 10.8 | 5.6 | 99–102 | 78 |
| 626 | 5-19 | C$_{15}$H$_{31}$N*HCl | 261.93 | 68.8 | 12.0 | 5.3 | 68.8 | 12.0 | 5.3 | 167–169 | 72 |
| 640 | 5-20 | C$_{12}$H$_{25}$N*HCl | 219.84 | 65.6 | 11.9 | 6.4 | 65.6 | 11.7 | 6.3 | 249–251 | 86 |
| 639 | 5-21 | C$_{13}$H$_{27}$N*HCl | 233.82 | 66.8 | 12.1 | 6.0 | 66.6 | 12.3 | 5.9 | 257–259 | 82 |
| 642 | 5-22 | C$_{13}$H$_{27}$N*HCl*H$_2$O | 251.82 | 62.0 | 12.0 | 5.6 | 62.0 | 12.0 | 5.5 | >210 | 98 |
| 645 | 5-23 | C$_{13}$H$_{29}$N*HCl | 247.85 | 67.8 | 12.2 | 5.7 | 67.6 | 12.3 | 5.6 | 205–207 | 89 |
| 644 | 5-24 | C$_{12}$H$_{25}$N*HCl | 219.84 | 65.6 | 11.9 | 6.4 | 65.4 | 11.9 | 6.2 | >250 | 83 |
| 662 | 5-25 | C$_{13}$H$_{27}$N*HCl*0.5H$_2$O | 242.84 | 64.3 | 12.0 | 5.8 | 64.9 | 12.0 | 5.7 | >250 | 64 |
| 580 | 5-26 | C$_{11}$H$_{23}$N*HCl | 205.81 | 64.2 | 11.3 | 6.8 | 64.1 | 11.4 | 6.9 | >230 | 50 |
| 557 | 5-27 | C$_{10}$H$_{21}$N*HCl | 191.75 | 62.6 | 11.6 | 7.3 | 62.3 | 11.6 | 7.2 | >250(dec.) | 70 |
| 641 | 5-28 | C7H15N*HCl | 149.7 | 56.2 | 10.8 | 9.4 | 55.9 | 11.0 | 9.2 | 283–285 | 89 |

TABLE 5

Spectral data of Amino-cyclohexane derivatives 5

| Compd. | $^1$H—NMR(CDCl$_3$, TMS)δ ppm |
|---|---|
| 5-1a | 0.89(3H, d, 6Hz); 0.9–1.4(3H, m); 1.44(3H, s); 1.5–2.3(6H, m); 8.3(3H, br s) |
| 5-1b | 0.90(3H, d, 5Hz); 1.46(3H, s); 1.0–2.3(9H, m); 8.3(3H, br s) |
| 5-2a | 0.87(3H, t, 7Hz); 1.45(3H, s); 1.0–2.3(11H, m); 8.35(3H, br s) |
| 5-2b | 0.87(3H, t, 7Hz); 1.46(3H, s); 1.0–2.2(11H, m); 8.3(3H, br s) |
| 5-3a | 0.86(3H, t, 6.5Hz); 0.95–1.4(7H, m); 1.45(3H, s); 1.5–2.2(6H, m); 8.3(3H, br s) |
| 5-3b | 0.85(3H, t, 7Hz); 1.47(3H, s); 0.95–2.2(3H, m); 8.3(3H, br s) |
| 5-4 | 0.96(3H, s); 1.05(3H, s); 1.50(3H, s); 1.50(3H, s); 1.1–1.95(8H, m); 8.25(3H, br s) |

TABLE 5-continued

Spectral data of Amino-cyclohexane derivatives 5

| Compd. | $^1$H—NMR(CDCl$_3$, TMS)δ ppm |
|---|---|
| 5-5 | 0.82(3H, t, 7Hz); 0.90 and 1.04(total 3H, both s); 1.48 and 1.50(total 3H, both s); 1.1–2.0(10H, m); 8.25(3H, br s) |
| 5-6 | 0.88(3H, m); 0.94 and 1.07(total 3H, both s); 1.49 and 1.52(total 3H, both s); 1.1–2.0(12H, m); 8.25(3H, br s) |
| 5-7 | 0.90(6H, d, 6Hz); 1.44 and 1.50(total 3H, both s); 0.95–2.4(8H, m); 8.25(3H, br s) |
| 5-8a | 0.90 and 0.91(total 6H, d, s); 1.23(3H, s); 1.44(3H, s); 0.95–2.3(7H, m); 8.2(3H, br s) |
| 5-9a | 0.83(s) and 0.87(m, total 9H); 1.47(3H, s); 1.0–2.2(9H, m); 8.15(3H, br s) |
| 5-9b | 0.7–1.0(m) and 0.89(s, total 9H); 1.55(3H, s); 1.05–2.2(9H, m); (3H, br s) |
| 5-10a | 0.7–0.95(m) and 0.86(s, total 9H); 1.51(3H, s); 0.95–2.3(11H, m); 8.2(3H, br s) |
| 5-10b | 0.7–1.0(m) and 0.90(s, total 9H); 1.54(3H, s); 1.05–2.1(11H, m); 8.2(3H, br s) |
| 5-11a | 0.8–1.0(m) and 0.91(s, total 6); 1.22(3H, s), 1.44(3H, s); 1.0–2.3(9H, m); 8.2(3H, br s) |
| 5-11b | 0.88(m) and 0.96(s, total 9H); 1.50(3H, s); 1.0–2.15(9H, m); 8.2(3H, br s) |
| 5-12a | 0.91(6H, m); 1.22(3H, s); 1.45(3H, s); 1.0–2.3(11H, m); 8.2(3H, br s) |
| 5-12b | 0.89(m); 0.97(s, total 9H); 1.54(3H, s); 10–2.2(11H, m); 8.2(3H, br s) |
| 5-13 | 1.02 and 1.07(total 12H, s); 1.26(2H, m); 1.62(3H, s); 1.71(4H, m) |
| 5-14 | 1.03 and 1.07(total 12H, s); 1.09(3H, t, 7Hz); 1.29(2H, s); 1.59 and 1.81(total 4H, d, 14Hz); 196(2H, q, 7Hz); 8.15(3H, br s) |
| 5-15 | 0.93(3H, t, 7Hz); 1.01 and 1.04(total 12H, s); 1.29(2H, s); 135–2.0(4H, m); 1.70(4H, m); 8.2(3H, br s) |
| 5-16 | 0.83(3H, m); 1.00, 1.02 and 1.07(total 9H, s); 1.2–1.5(4H, m); 1.59 and 1.63(total 3H, both s); 1.70(4H, m); 8.25(3H, br s) |
| 5-17 | 0.87(3H, m); 1.0–1.1(9H, m); 1.1–1.4(6H, m); 1.60 and 1.64(total 3H, both s); 1.70(4H, m); 8.25(3H, br s) |
| 5-18 | 0.78(6H, t, 7Hz); 1.04(6H, s); 1.27(2H, m); 1.40(4H, m); 1.59(3H, s); 1.6–1.8(4H, m); 8.25(3H, br s) |
| 5-19 | 0.87(6H, m); 1.04(6H, s); 1.1–1.5(10H, m); 1.60(3H, s); 1.5–1.95(4H, m); 8.2(3H, br s) |
| 5-20 | 1.00 and 1.11(total 12H, s); 1.29(2H, m); 1.57(3H, s); 1.72(4H, dd, 14Hz); 2.56(3H, t, 6Hz); 9.2 ppm(2H, br s). |
| 5-21 | 0.98 and 1.11(total 12H, s); 1.29(2H, m); 1.58(3H, s); 1.61(3H, t, 7Hz); 1.82(4H, m); 3.0(2H, m); 9.1 ppm(2H, br s) |
| 5-22 | 1.03 and 1.12(total 12H, s); 1.32(2H, m); 1.45(3H, s); 1.64 and 1.97(total 4H, d, 14Hz); 2.69(6H, d, 5Hz) |
| 5-23 | 0.85(6H, s); 1.02(6H, s); 0.6–1.95(7H, m); 1.46(6H, s); 1.60(2H, d, 5Hz); 8.35(3H, br s) |
| 5-24 | 0.87(6H, s); 0.98(6H, s); 0.6–1.85(9H, m); 3.02(2H, m); 8.30(3H, br s) |
| 5-25 | 0.96(6H, s); 1.02(6H, s,); 1.07(3H, s); 1.18(6H, s); 1.73(2H, m); 3.03(2H, m); 8.28(3H, br s) |
| 5-26 | 0.97(12H, br s); 1.0–2.2(7H, m); 2.80(2H, m); 8.35 ppm(3H, br s). |
| 5-27 | 0.97(6H, s); 1.04(6H, s); 1.12(1H, d, 13.7Hz); 1.2–1.4(5H, m); 1.92(2H, d, 12.3Hz); 3.41(1H, m); 8.30(3H, br s) |
| 5-28 | 1.47(3H, s) 1.2–2.2(10H, m); 8.3(3H, br s) |

TABLE 6

Basic Structure of the amino- and aminoalkylcyclohexanes.

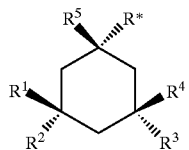

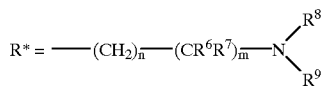

n + m = 0, 1, 2
$R^1 - R^9$ = lower alkyl

| Mrz 2/ | Compd | $R^1$ | $R^2$ | $R^3$ | $R^4$ | $R^5$ | R* |
|---|---|---|---|---|---|---|---|
| 625 | 5-1a | H | H | H | Me | Me | NH$_2$ |
| 631 | 5-1b | H | H | Me | H | Me | NH$_2$ |
| 629 | 5-2a | H | H | H | Et | Me | NH$_2$ |
| 630 | 5-2b | H | H | Et | H | Me | NH$_2$ |
| 627 | 5-3a | H | H | H | Pr | Me | NH$_2$ |
| 628 | 5-3b | H | H | Pr | H | Me | NH$_2$ |
| 621 | 5-4 | H | H | Me | Me | Me | NH$_2$ |
| 620 | 5-5 | H | H | Me (Et) | Et (Me) | Me | NH$_2$ |
| 617 | 5-6 | H | H | Me (Pr) | Pr (Me) | Me | NH$_2$ |
| 616 | 5-7 | Me (H) | H (Me) | H (Me) | Me (H) | Me | NH$_2$ |
| 643 | 5-8a | Me | Me | Me | H | Me | NH$_2$ |
| 607 | 5-8a | Me | Me | H | Me | Me | NH$_2$ |
| 622 | 5-9a | Me | H | Et | Me | Me | NH$_2$ |
| 624 | 5-9b | H | Me | Me | Et | Me | NH$_2$ |
| 618 | 5-10a | Me | H | Pr | Me | Me | NH$_2$ |
| 619 | 5-10b | H | Me | Me | Pr | Me | NH$_2$ |
| 633 | 5-11a | Me | Me | H | Et | Me | NH$_2$ |
| 632 | 5-11b | Me | Me | Et | H | Me | NH$_2$ |
| 635 | 5-12a | Me | Me | H | Pr | Me | NH$_2$ |
| 634 | 5-12b | Me | Me | Pr | H | Me | NH$_2$ |

TABLE 6-continued

Basic Structure of the amino- and aminoalkylcyclohexanes.

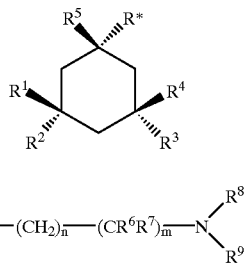

$$R^* = \text{———}(CH_2)_{\overline{n}}\text{—}(CR^6R^7)_{\overline{m}}\text{—}N\begin{smallmatrix}R^8\\R^9\end{smallmatrix}$$

n + m = 0, 1, 2
$R^1 - R^9$ = lower alkyl

| Mrz 2/ | Compd | $R^1$ | $R^2$ | $R^3$ | $R^4$ | $R^5$ | R* |
|---|---|---|---|---|---|---|---|
| 579 | 5-13 | Me | Me | Me | Me | Me | $NH_2$ |
| 600 | 5-14 | Me | Me | Me | Me | Et | $NH_2$ |
| 601 | 5-15 | Me | Me | Me | Me | Pr | $NH_2$ |
| 615 | 5-16 | Me | Me | Me (Et) | Et (Me) | Me | $NH_2$ |
| 614 | 5-17 | Me | Me | Me (Pr) | Pr (Me) | Me | $NH_2$ |
| 623 | 5-18 | Me | Me | Et | Et | Me | $NH_2$ |
| 626 | 5-19 | Me | Me | Pr | Pr | Me | $NH_2$ |
| 640 | 5-20 | Me | Me | Me | Me | Me | NHMe |
| 639 | 5-21 | Me | Me | Me | Me | Me | NHEt |
| 642 | 5-22 | Me | Me | Me | Me | Me | N(Me)2 |
| 645 | 5-23 | Me | Me | Me | Me | H | $CH_2CMe_2NH_2$ |
| 644 | 5-24 | Me | Me | Me | Me | H | $CH_2CH_2NH_2$ |
| 662 | 5-25 | Me | Me | Me | Me | Me | $CH_2CH_2NH_2$ |
| 580 | 5-26 | Me | Me | Me | Me | H | $CH_2NH_2$ |
| 557 | 5-27 | Me | Me | Me | Me | H | $NH_2$ |
| 641 | 5-28 | H | H | H | H | Me | $NH_2$ |
| 705 | infra | Me | Me | Me | Me | Me | N-pyrrolidine |

PHARMACEUTICAL COMPOSITIONS

The active ingredients of the invention, together with one or more conventional adjuvants, carriers, or diluents, may be placed into the form of pharmaceutical compositions and unit dosages thereof, and in such form may be employed as solids, such as coated or uncoated tablets or filled capsules, or liquids, such as solutions, suspensions, emulsions, elixirs, or capsules filled with the same, all for oral use; in the form of suppositories or capsules for rectal administration or in the form of sterile injectable solutions for parenteral (including intravenous or subcutaneous) use. Such pharmaceutical compositions and unit dosage forms thereof may comprise conventional or new ingredients in conventional or special proportions, with or without additional active compounds or principles, and such unit dosage forms may contain any suitable effective amount of the active ingredient commensurate with the intended daily dosage range to be employed. Tablets containing twenty (20) to one hundred (100) milligrams of active ingredient or, more broadly, ten (10) to two hundred fifty (250) milligrams per tablet, are accordingly suitable representative unit dosage forms.

METHOD OF TREATING

Due to their high degree of activity and their low toxicity, together presenting a most favorable therapeutic index, the active principles of the invention may be administered to a subject, e.g., a living animal (including a human) body, in need thereof, for the treatment, alleviation, or amelioration, palliation, or elimination of an indication or condition which is susceptible thereto, or representatively of an indication or condition set forth elsewhere in this application, preferably concurrently, simultaneously, or together with one or more pharmaceutically-acceptable excipients, carriers, or diluents, especially and preferably in the form of a pharmaceutical composition thereof, whether by oral, rectal, or parental (including intravenous and subcutaneous) or in some cases even topical route, in an effective amount. Suitable dosage ranges are 1–1000 milligrams daily, preferably 10–500 milligrams daily, and especially 50–500 milligrams daily, depending as usual upon the exact mode of administration, form in which administered, the indication toward which the administration is directed, the subject involved and the body weight of the subject involved, and the preference and experience of the physician or veterinarian in charge.

EXAMPLES OF REPRESENTATIVE PHARMACEUTICAL COMPOSITIONS

With the aid of commonly used solvents, auxiliary agents and carriers, the reaction products can be processed into tablets, coated tablets, capsules, drip solutions, suppositories, injection and infusion preparations, and the like and can be therapeutically applied by the oral, rectal, parenteral, and additional routes. Representative pharmaceutical compositions follow.

(a) Tablets suitable for oral administration which contain the active ingredient may be prepared by conventional tabletting techniques.

(b) For suppositories, any usual suppository base may be employed for incorporation thereinto by usual procedure of the active ingredient, such as a polyethyleneglycol which is a solid at normal room temperature but which melts at or about body temperature.

(c) For parental (including intravenous and subcutaneous) sterile solutions, the active ingredient together with conventional ingredients in usual amounts are employed, such as for example sodium chloride and double-distilled water q.s., according to conventional procedure, such as filtration, aseptic filling into ampoules or IV-drip bottles, and autoclaving for sterility.

Other suitable pharmaceutical compositions will be immediately apparent to one skilled in the art.

The following examples are again given by way of illustration only and are not to be construed as limiting.

EXAMPLE 1

Tablet Formulation

A suitable formulation for a tablet containing 10 milligrams of active ingredient is as follows:

|  | Mg. |
|---|---|
| Active Ingredient | 10 |
| Lactose | 63 |
| Microcrystalline Cellulose | 21 |
| Talcum | 4 |
| Magnesium stearate | 1 |
| Colloidal silicon dioxide | 1 |

EXAMPLE 2

Tablet Formulation

Another suitable formulation for a tablet containing 100 mg is as follows:

|  | Mg. |
|---|---|
| Active Ingredient | 100 |
| Potato starch | 20 |
| Polyvinylpyrrolidone | 10 |
| Film coated and colored. The film coating material consists of: | |
| Lactose | 100 |
| Microcryst. Cellulose | 80 |
| Gelatin | 10 |
| Polyvinylpyrrolidone, crosslinked | 10 |
| Talcum | 10 |
| Magnesium stearate | 2 |
| Colloidal silicon dioxide | 3 |
| Color pigments | 5 |

EXAMPLE 3

Capsule Formulation

A suitable formulation for a capsule containing 50 milligrams of active ingredient is as follows:

|  | Mg. |
|---|---|
| Active Ingredient | 50 |
| Corn starch | 20 |
| Dibasic calcium phosphate | 50 |
| Talcum | 2 |
| Colloidal silicon dioxide | 2 | filled in a gelatin capsule.

EXAMPLE 4

Solution for injection

A suitable formulation for an injectable solution containing one percent of active ingredient is as follows:

| Active Ingredient mg | 12 |
|---|---|
| Sodium chloride mg | 8 |
| Sterile water to make ml | 1 |

EXAMPLE 5

Liquid oral formulation

A suitable formulation for 1 liter of a liquid mixture containing 2 milligrams of active ingredient in one milliliter of the mixture is as follows:

|  | G. |
|---|---|
| Active Ingredient | 2 |
| Saccharose | 250 |
| Glucose | 300 |
| Sorbitol | 150 |
| Orange flavor | 10 |
| Sunset yellow. | |
| Purified water to make a total of 1000 ml. | |

EXAMPLE 6

Liquid oral formulation

Another suitable formulation for 1 liter of a liquid mixture containing 20 milligrams of active ingredient in one milliliter of the mixture is as follows:

|  | G. |
|---|---|
| Active Ingredient | 20 |
| Tragacanth | 7 |
| Glycerol | 50 |
| Saccharose | 400 |
| Methylparaben | 0.5 |
| Propylparaben | 0.05 |
| Black currant-flavor | 10 |
| Soluble Red color | 0.02 |
| Purified water to make a total of 1000 ml. | |

EXAMPLE 7

Liquid oral formulation

Another suitable formulation for 1 liter of a liquid mixture containing 2 milligrams of active ingredient in one milliliter of the mixture is as follows:

|  | G. |
|---|---|
| Active Ingredient | 20 |
| Saccharose | 400 |
| Bitter orange peel tincture | 20 |
| Sweet orange peel tincture | 15 |
| Purified water to make a total of 1000 ml. | |

EXAMPLE 8

Aerosol formulation 180 g aerosol solution contain:

|  | G. |
|---|---|
| Active Ingredient | 10 |
| Oleic acid | 5 |
| Ethanol | 81 |
| Purified Water | 9 |
| Tetrafluoroethane | 75 |

15 ml of the solution are filled into aluminum aerosol cans, capped with a dosing valve, purged with 3.0 bar.

EXAMPLE 9

TDS formulation 100 g solution contain:

|  | G. |
|---|---|
| Active Ingredient | 10 |
| Ethanol | 57.5 |
| Propyleneglycol | 7.5 |
| Dimethylsulfoxide | 5.0 |
| Hydroxyethylcellulose | 0.4 |
| Purified water | 19.6 |

1.8 ml of the solution are placed on a fleece covered by an adhesive backing foil. The system is closed by a protective liner which will be removed before use.

EXAMPLE 10

Nanoparticle formulation 10 g of polybutylcyanoacrylate nanoparticles contain:

|  | G. |
|---|---|
| Active Ingredient | 1.0 |
| Poloxamer | 0.1 |
| Butylcyanoacrylate | 8.75 |

-continued

|  | G. |
|---|---|
| Mannitol | 0.1 |
| Sodiumchloride | 0.05 |

Polybutylcyanoacrylate nanoparticles are prepared by emulsion polymersiation in a water/0.1 N HCl/ethanol mixture as polymerisation medium. The nanoparticles in the suspension are finally lyophilized under vacuum.

PHARMACOLOGY—SUMMARY

The active principles of the present invention, and pharmaceutical compositions thereof and method of treating therewith, are characterized by unique advantageous and unpredictable properties, rendering the "subject matter as a whole", as claimed herein, unobvious. The compounds and pharmaceutical compositions thereof have exhibited, in standard accepted reliable test procedures, the following valuable properties and characteristics:

They are systemically-active, uncompetitive NMDA receptor antagonists with rapid blocking/unblocking kinetics and strong voltage dependency and are accordingly of utility in the treatment, elimination, palliation, alleviation, and amelioration of responsive conditions, by application or administration to the living animal host for the treatment of a wide range of CNS disorders which involve disturbances of glutamatergic transmission.

PHARMACOLOGY

In vitro

Receptor Binding Studies

Male Sprague-Dawley rats (200–250 g) were decapitated and their brains were removed rapidly. The cortex was dissected and homogenized in 20 volumes of ice-cold 0.32 M sucrose using a glass-Teflon homogenizer. The homogenate was centrifuged at 1000×g for 10 minutes. The pellet was discarded and the supernatant centrifuged at 20,000×g for 20 minutes. The resulting pellet was re-suspended in 20 volumes of distilled water and centrifuged for 20 minutes at 8000×g. Then the supernatant and the buffy coat were centrifuged three times (48,000×g for 20 minutes) in the presence of 50 mM Tris-HCl, pH 8.0. All centrifugation steps were carried out at 4° C. After resuspension in 5 volumes of 50 mM Tris-HCl, pH 8.0 the membrane suspension was frozen rapidly at −80° C. On the day of assay the membranes were thawed and washed four times by resuspension in 50 mM Tris-HCl, pH 8.0 and centrifugation at 48,000×g for 20 minutes. The final pellet was suspended in assay buffer. The amount of protein in the final membrane preparation was determined according to the method of Lowry with some modifications. The final protein concentration used for our studies was between 250–500 µg/ml.

Membranes were re-suspended and incubated in 50 mM Tris-HCl, pH 8.0. Incubations were started by adding [$^3$H]-(+)-MK-801 (23.9 Ci/mmol, 5nM) to vials with glycine (10 µM), glutamate (10 µM), and 0.1–0.25 mg protein (total volume 0.5 ml) and various concentrations of the agents tested (10 concentrations in duplicates). The incubations were continued at room temperature for 120 minutes, equilibrium always being achieved under the conditions used. Non-specific binding was defined by the addition of unlabeled MK-801 (10 µM). Incubations were terminated using a Millipore filter system. The samples were rinsed three times with 2.5 ml ice cold assay buffer over glass fiber filters obtained from Schleicher & Schuell under a constant vacuum. Filtration was performed as rapidly as possible. Following separation and rinse, the filters were placed into scintillation liquid (5 ml; Ultima Gold) and radioactivity retained on the filters was determined with a conventional liquid scintillation counter (Hewlett Packard, Liquid Scintillation Analyser).

Patch Clamp

Hippocampi were obtained from rat embryos (E20 to E21) and were then transferred to calcium and magnesium free Hank's buffered salt solution (Gibco) on ice. Cells were mechanically dissociated in 0.05% DNAase/0.3% ovomucoid (Sigma) following an 8 minute pre-incubation with 0.66% trypsin/0.1% DNAase (Sigma). The dissociated cells were then centrifuged at 18×g for 10 minutes, re-suspended in minimum essential medium (Gibco) and plated at a density of 150,000 cells $cm^{-2}$ onto poly-L-lysine (Sigma)-precoated plastic petri dishes (Falcon). The cells were nourished with $NaHCO_3$/HEPES-buffered minimum essential medium supplemented with 5% fetal calf serum and 5% horse serum (Gibco) and incubated at 37° C. with 5% $CO_2$ at 95% humidity. The medium was exchanged completely following inhibition of further glial mitosis with cytosine-β-D-arabinofuranoside (20 μM Sigma) after about 7 days in vitro. Thereafter the medium was exchanged partially twice weekly.

Patch clamp recordings were made from these neurones with polished glass electrodes (4–6 mΩ) in the whole cell mode at room temperature (20–22° C.) with the aid of an EPC-7 amplifier (List). Test substances were applied by switching channels of a custom-made fast superfusion system with a common outflow (10–20 ms exchange times). The contents of the intracellular solution were as follows (mM): CsCl (120), TEACl (20), EGTA (10), $MgCl_2(1)$, $CaCl_2$-(0.2), glucose (10), ATP(2), cAMP (0.25); pH was adjusted to 7.3 with CsOH or HCl. The extracellular solutions had the following basic composition (mM): NaCl (140), KCl (3), $CaCl_2$ (0.2), glucose (10), HEPES (10), sucrose (4.5), tetrodotoxin (TTX $3*10^{-4}$). Glycine (1μM) was present in all solutions: a concentration sufficient to cause around 80–85% activation of glycine, receptors. Only results from stable cells were accepted for inclusion in the final analysis, i.e., following recovery of responses to NMDA by at least 75% of their depression by the antagonists tested.

Excitotoxicity

Cortical neurones were obtained from cerebral cortices of 17/18 day old fetal rats (Wistar), in general following the dissociation procedure described by [23]. After short trypsinization and gentle trituration with fire-polished Pasteur pipettes, the cell suspension was washed by centrifugation. Cells were suspended in serum-free Neurobasal medium with B27 supplement (GIBCO) before plating onto poly-L-lysine (Sigma; 0.2mg/ml, 20 h, 4° C.) and laminin (Sigma; 2 μg/ml, 1h, 37° C.)-coated 96-well plates (Falcon, Primaria) at a density of $5\times10^4$ cells/well. Cortical neurones were maintained at 37° C. in humidified 10% $CO_2$/90% air. One day after plating, 5 μM cytosine-β-D-arabinofuranoside (Sigma) was added to each well for inhibition of glial cell proliferation. The medium was changed first after 4 days in vitro and then every 4 days by replacing ⅔ of the medium with astrocyte-conditioned medium. Cortical neurones between day 12 and 14 in culture were used for the experiments.

New-born rat astrocytes were isolated non-enzymatically according to the method of [24]. Briefly, both hemispheres were dissected from 2-day-old rats, passed through an 80 μm gauze, and triturated with Pasteur pipettes. Cell suspension was made in Dulbecco's modified essential medium (DMEM, Gibco) supplemented with 10% fetal calf serum (FCS, Hyclone), 2mM glutamine (Gibco) and 50 μg/ml gentamycin and transferred into untreated, plastic culture flasks (Corning; 75 $cm^3$). Two days after plating the flasks were shaken for 10 minutes on a rotary platform (150 U/min) to remove microglial cells. The cultures were grown to confluency within 14 days, and the culture medium was changed twice weekly. Thereafter, the glial monolayers were extensively washed with serum-free Neurobasal medium (Gibco) to remove the serum. Flasks were then shaken several times to remove oligodendrocytes and neurones. To obtain conditioned medium from primary astrocytes, the cultures were incubated with fresh Neurobasal medium supplemented with B27 and glutamine. Every 2–3 days the conditioned medium was collected and replaced by fresh medium up to 4 times.

Exposure to EAA was performed in serum-free Neurobasal medium containing 100 μM glutamate and the drug to be tested. After 20 h of incubation, the cytotoxic effect was morphologically examined under a phase contrast microscope and biochemically quantified by measuring cell viability with the MTT test (Promega). This calorimetric assay measures the reduction of a tetrazolium component (MTT) into an insoluble formazan product by the mitochondria of living cells. After incubation of the cortical neurones with the dye solution for approximately 1–4 hours, a solubilization solution was added to lyse the cells and solubilize the colored product (incubation overnight at 37° C., 10% $CO_2$, 90% RH). These samples were then read using an Elisa plate reader (Thermomax, MWG Biotech) at a wavelength of 570 nm. The amount of color produced was directly proportional to the number of viable cells.

In vivo

Anticonvulsive activity

NMR female mice (18–28 g) housed 5 per cage were used for the maximal electroshock (MES) and motor impairment tests. All animals were kept with water and food ad libitum under a 12 hour light-dark cycle (light on at 6 a.m.) and at a controlled temperature (20±0.5° C.). All experiments were performed between 10 a.m. and 5 p.m. Tested agents were injected 30 min. i.p. before the induction of convulsions if not stated otherwise (see below). All compounds were dissolved in 0.9% saline.

The MES test was performed together with tests for myorelaxant action (traction reflex) and motor coordination (rotarod). For the traction reflex test mice were placed with their forepaws on a horizontal rod and were required to place all 4 paws on the wire within 10 seconds. To test ataxia (motor coordination) mice were placed on rotarod (5 rpm) and were required to remain on the rod for 1 minute. Only mice not achieving the criteria in all three repetitions of each test were considered to exhibit myorelaxation or ataxia respectively. These tests were followed by MES (100 Hz, 0.5 second shock duration, 50 mA shock intensity, 0.9 ms impulse duration, Ugo Basile) applied through corneal electrodes. The presence of tonic convulsions was scored (tonic extension of hind paws with minimum angle to the body of 90°). The aim was to obtain $ED_{50}$s for all parameters scored (anticonvulsive activity and motor side effects) with use of the Litchfield Wilcoxon test for quantal dose responses. Division of the $ED_{50}$ for side effects (ataxia or myorelaxation) by the $ED_{50}$ for antagonism of electroshock convulsions was used as a therapeutic index (TI).

Statistical analysis $IC_{50}$s in patch clamp, excitotoxicity, and binding studies were calculated according to the four parameter alogistic equation using the Grafit computer program (Erithacus Software, England). Ki value for binding studies were then determined according to Cheng and Prusoff. Binding values presented are means ±SEM of 3–5 determinations (each performed in duplicate).

4–7 doses of antagonists were tested in each of the in vivo tests (5–8 animals per dose) to allow calculation of graded $ED_{50}s$ according to probit analysis (Litchfield and Wilcoxon) with correction for 0% to 100% effects. $ED_{50}s$ are presented with 95% confidence limits (CI). Pearson product moment correlation analysis (Sigma Stat, Jandel Scientific) was used to compare in vitro potencies and in vivo anticonvulsant activity.

RESULTS

Binding

All cyclohexanes displaced [$^3$H]-(+)-MK-801 binding to rat cortical membranes with $IC_{50}s$ of between 4 and 150 μM whilst Ki values as assessed with the Cheng-Prussoff equation were 2 fold lower (see Table 7).

Patch Clamp

Steady-state inward current responses of cultured hippocampal neurones to NMDA (200 μM with glycine 1 μM at −70 mV) were antagonized by the tested cyclohexanes with $IC_{50}s$ of 1.3–99 μM (Table 7). Peak and steady-state currents were affected to a similar degree making it unlikely that their effects were mediated at the glycine$_B$ site. Strong support for the uncompetitive nature of this antagonism was provided by the clear use- and voltage-dependency of their blockade. The weaker antagonists showed faster kinetics and stronger voltage-dependency.

Excitotoxicity

Low μM concentrations of most cyclohexanes were effective neuroprotectants in vitro, with Mrz 2/579 seeming to be most potent in this regard (see Table 7). With most compounds full protection was obtained with 20 μM.

In vivo

Anticonvulsive activity

All cyclohexane derivatives inhibited MES-induced convulsions in mice with $ED_{50}s$ ranging from 3.6 to 50 mg/kg i.p. (Table 7). Selected compounds were also tested against PTZ- and NMDA-induced convulsions (see [20,21] for methods) and showed comparable potency to the MES test (e.g., Mrz 2/579 had $ED_{50}s$ in the PTZ- and NMDA tests of 5.5 and 3.7 mg/kg respectively). Their anticonvulsive potency was increased following i.v. administration (e.g., Mrz 2/579 $ED_{50}$=2.5 mg/kg). Mrz 2/579 was also active following s.c. and somewhat less potent following p.o. administration ($ED_{50}s$ of 4.6 and 13.7 mg/kg respectively). At doses within the anticonvulsive range, myorelaxation (traction test) and ataxia (rotarod test) were observed with some cyclohexanes. For the majority of them, no acute lethality was seen at up to 50 mg/kg.

Correlation Analysis

There was a very good cross correlation between all three in vitro assays (all corr. coeffs.>0.70, p<0.001). There was also a good correlation between potencies in antagonizing NMDA-induced inward currents and protection against NMDA-induced toxicity in vitro with anticonvulsive activity in vivo (corr. coeffs.>0.56, p<0.01).

TABLE 7

| Mrz2/ | [$^3$H]MK-801 $IC_{50}$(μM)(μM) | SEM | Patch Clamp $IC_{50}$(μM) | SEM | Glut. Tox. $IC_{50}$(μM) | SD | MES $ED_{50}$ mg/kg | C.I. |
|---|---|---|---|---|---|---|---|---|
| 557 | 17.6 | 0.9 | 18.5 | 2.7 | 6.7 | 2.0 | 43.9 | 35.6–54.1 |
| 579 | 1.9 | 0.1 | 1.3 | 0.02 | 2.2 | 0.0 | 3.6 | 2.2–6.1 |
| 580 | 15.9 | 0.8 | 12.9 | 0.4 | 5.6 | 0.6 | 27.3 | 12.8–64 |
| 600 | 24 | 0.1 | 3.7 | 0.2 | 2.1 | 0.2 | 22.6 | 43.0–197 |
| 601 | 7.4 | 0.7 | 10.5 | 0.8 | 3.5 | 0.3 | 15.6 | 10.4–23.4 |
| 607 | 8.2 | 0.3 | 13.6 | 1.5 | 10.1 | 2.2 | 22.9 | 18.3–28.7 |
| 614 | 13.6 | 1.3 | 13.9 | 1.9 | >10 | | 23.5 | 15.7–34.9 |
| 615 | 2.5 | 0.1 | 2.9 | 0.1 | 2.3 | 0.1 | 6.1 | 3.4–10.7 |
| 616 | 150 | 0.4 | 34.2 | 4.6 | 9.1 | 2.1 | 24.0 | 15.6–36.8 |
| 617 | 51.8 | 3.9 | 57.4 | 7.3 | >70 | | 54.9 | 42.9–70.4 |
| 618 | 32.7 | 2.4 | 43.7 | 9.4 | 17.6 | 2.9 | 24.0 | 9.6–59.5 |
| 619 | 72.1 | 6.7 | 60.8 | 5.4 | 30.9 | 2.9 | 44.6 | 32.0–62.3 |
| 620 | 32.2 | 2.1 | 99.0 | 10.4 | 38.4 | 1.6 | 41.3 | 32.9–51.7 |
| 621 | 36.7 | 4.4 | 92.4 | 19.0 | >100 | | 36.9 | 22.6–60.3 |
| 622 | 150 | 0.6 | 64.8 | 11.7 | 19.3 | 8.1 | 21.0 | 16.1–27.5 |
| 623 | 3.3 | 0.2 | 3.7 | 0.7 | 4.5 | 0.6 | 13.1 | 9.9–17.2 |
| 624 | 15.4 | 1.2 | 31.0 | 3.6 | 2.7 | 0.6 | 47.2 | 41.8–53.2 |
| 625 | 46.8 | 8.1 | 244.9 | 40.1 | 39.4 | 6.3 | 129.8 | 42.5–395.6 |
| 626 | 11.6 | 1.5 | 9.6 | 2.0 | 19.0 | 3.3 | 41.2 | 29.9–56.7 |
| 627 | 70.3 | 3.3 | 209.7 | 1.0 | 26.6 | 5.7 | 43.9 | 30.3–63.7 |
| 628 | 35.6 | 4.4 | 125.5 | 0.8 | 27.3 | 4.5 | 73.2 | 33.6–159.4 |
| 629 | 39.4 | 2.4 | 218.6 | 1.6 | >300 | | 58.5 | 38.3–89.2 |
| 630 | 443 | 3.8 | >100 | | >100 | | >30 | |
| 631 | 69.7 | 8.6 | >100 | | >100 | | 30.00 | |
| 632 | 2.0 | 0.2 | 6.4 | 0.6 | 10.9 | 0.4 | 11.04 | 7.7–15.8 |
| 633 | 6.6 | 0.5 | 13.9 | 3.2 | 5.4 | 0.9 | 8.78 | 3.6–21.4 |
| 634 | 15.5 | 1.0 | 10.8 | 2.6 | 19.0 | 3.5 | >30 | |
| 635 | 7.8 | 0.4 | 21.0 | 4.6 | 8.2 | 1.4 | 31.59 | 21.3–46.6 |
| 639 | 3.3 | 0.3 | 7.4 | 1.0 | 5.7 | 0.4 | 5.5 | 3.6–9.0 |
| 640 | 3.7 | 0.6 | 14.6 | 1.2 | 8.3 | 0.4 | 8.2 | 5.7–11.8 |
| 641 | 184.5 | 26.7 | >100 | | >100 | | >50 | |
| 642 | 10.2 | 1.6 | 42.5 | 6.5 | 29.3 | 3.3 | 8.04 | 5.1–12.7 |
| 643 | 3.6 | 0.5 | 13.5 | 1.7 | 12.0 | 0.9 | 16.65 | 10.8–32.2 |
| 644 | 3.8 | 3.7 | 4.1 | 1.8 | 4.3 | 0.4 | 52.98 | 27.8–100.8 |
| 645 | 85.1 | 30.6 | 20.4 | 3.6 | >100 | | 65.61 | 43.8–98.2 |
| Memantine | 0.7 | 0.11 | 2.3 | 0.3 | 1.3 | 0.7 | 6.9 | 5.4–8.8 |
| Amantadine | 20.4 | 5.4 | 71.0 | 11.1 | 20.7 | 0.7 | 184.0 | 122–279 |
| MK-801 | 0.0026 | 0.0002 | 0.14 | 0.10 | 0.012 | 0.002 | 0.16 | 0.13–0.21 |

Effects of cyclohexane derivatives and standard uncompetitive NMDA receptor antagonists on [$^3$H]-(+)-MK-801 binding, NMDA induced currents in patch clamp experiments, glutamate toxicity in cultured cortical neurones and MES-convulsions in vivo. Binding Ki values are means TSEM of 3–5 experiments. $IC_{50}$s (+SEM) in patch clamp and glutamate toxicity experiments were determined from data from at least 3 concentrations producing between 15 and 85% inhibition and at least 5 cells per concentration. For MES-induced convulsions, values are $ED_{50}$s in mg/kg (95% confidence limits are shown in parentheses).

In addition, due at least in part to their amine substituent, the compounds of the present invention are =also effective in non-NMDA indications, exhibiting immuno-modulatory activity, antimalaria potency, anti-Borna virus activity, and anti-Hepatitis C activity.

ADDITIONAL EXAMPLES AND PHARMACOLOGICAL UPDATES

Further 1-aminoalkylcyclohexane compounds, wherein the 1-amino group is cyclic, that is, wherein $R^8$ and $R^9$ together represent lower-alkylene —(CH2)x— wherein x is 2 to 5, inclusive, thereby presenting the 1-amino group —$NR^8 R^9$ in the form of a cyclic amine, are prepared in the following manner:

Preparation of N-(3-Cyanopropyl)-1,3,3,5,5-Pentamethylcyclohexylamine (2)

A mixture of 1,3,3,5,5-pentamethylcyclohexylamine hydrochloride (1) (2–06 g, 10 mmol) 4-bromobutyronitrile (1.55 g. 10.5 mmol) and sodium carbonate (3.18 g, 30 mmol) in tetrahydrofuran (50 ml) was refluxed for 85 h, the poured into water (100 ml) and extracted with ether (3*30 ml). The combined organic phases were washed with brine (20 ml) and dried over $K_2CO_3$. The solution was filtered and evaporated and the crude product was purified by chromatography on silica gel, eluting with hexane-ether (10:1), (6:1), (4:1) to give product 2 (1.86 g, 86%) as an colorless oil.

PMR spectrum: ($CDCl_3$, TMS) δ: 0.87 (6H, s, c-Hex 3,5-$CH_3$); 1.06 (3H, s, c-Hex 1-$CH_3$); 1.18 (6H, s, 3,5-$H_3$); 0.9–1.6 (7H, m, c-Hex ring protons and NH); 1.75 (2H, m, —$CH_2$—); 2.43 (2H, t, J=7 Hz, $CH_2$N) and 2.66 ppm. (2H, t, J=7 Hz, $CH_2$CN).

Preparation of MRZ 2/705. namely: N-(1,3,3,5,5-Pentamethylcyclohexyl) pyrrolidine hydrochloride (3)

N-(3-Cyanopropyl)-1,3,3,5,5-pentamethylcyclohexylamine (2) (1.2 g, 5.1 mmol) in ethanol (120 ml) and conc. HCl (4 ml) was hydrogenated over 10% Pd/C (250 mg) at 7 bar for 40 h (after 24 h additional portion of catalyst (260 mg) was added). The catalyst was removed by filtration through celite pad and solvent evaporated. The residue was treated with acetonitrile, the solids filtered off and the filtrate evaporated. The crude product vas crystallized from ether to give N-(1,3,3,5,5-pentamethylcyclohexyl) pyrrolidine hydrochloride (3) (0.67 g, 49%) with m.p. 156–158° C.

PMR spectrum: (DMSO-$d_6$, TMS) δ: 0.97 (6H, s, 3,5-$CH_3$); 1.11 (6H, s, 3,5-$CH_3$); 0.8–1.4 (2H, cyclohexane 4-$CH_2$) 1.41 (3H, s, 1-$CH_3$); 1.69 (4H, m, cyclohexane 2,6-$CH_2$); 1.84 (4H, m, pyrrolidine 3,4-$CH_2$) 3.20 (4H, m, pyrrolidine 2,5-$CH_2$); 10.9 ppm (1H, br s, $NH^+$). Elemental analysis: $C_{15}H_{29}N*HCl*0.5H_2O$: Found (%) C, 67.7; H, 11.5; N, 5.5. Calculated (%) C, 67.0; H, 11.6; N, 5.2.

Additional 1-cyclic amino compounds are prepared in the same manner starting from the selected alkyl-substituted cyclohexylamine, usually in the form of an acid addition salt such as the hydrochloride, and the selected w-bromoalkylnitrile, such as 4-bromobutyronitrile, 3-bromopropionitrile, 2-bromoacetonitrile, and 5-bromovaleronitrile, in the manner of the preceding preparation, first to produce the selected N-ω-cyanoalkyl-alkylcyclohexylamine compound and then to cyclize the N-ω-cyanoalkyl-alkylcyclohexylamine compound into the resulting N-(alkylcyclohexyl) cyclic amine compound, namely, the pyrrolidine, piperidine, or other cyclic amine compound, wherein the nitrogen atom and $R^8$ and $R^9$ together form the cyclic amine moiety, $R^8$ and $R^9$ together representing a lower-alkylene chain of the formula —$(CH_2)_x$— wherein x is 2 to 5, inclusive.

Thus N-(1,3,3,5,5-pentamethylcyclohexyl) piperidine hydrochloride or other acid addition salt and numerous other lower-alkyl substituted cyclohexanes having a 1-pyrrolidino or 1-piperidino group or other 1-cyclic amino group are prepared according to the invention, depending upon the ω-bromoalkylnitrile and the alkyl-substituted cyclohexylamine starting materials selected for the reaction.

UPDATED PHARMACOLOGICAL TABLES

The following Tables 8 and 9 present updated pharmacological results with various of the compounds of the present invention. The Tables show the following:

TABLE 8

| MRZ2/ | MES $ED_{50}$ mg/kg i.p. | | TI Tract | TI Rot. | Min Lethality mg/kg i.p. |
|---|---|---|---|---|---|
| 557 | 43.9 | (35.6–54.1) | 1.0 | 1.4 | >70 |
| 579 | 3.6 | (2.2–6.1) | 2.9 | 5.0 | 108 |
| 580 | 27.3 | (12.8–64) | 1.6 | 1.3 | 50 |
| 600 | 22.6 | (10.4–23.2) | 0.6 | 0.9 | 50 |
| 601 | 15.6 | (10.4–23.4) | 1.5 | 1.5 | 50 |
| 607 | 22.9 | (18.3–28.7) | 1.3 | 1.7 | 50 |
| 614 | 23.5 | (15.7–34.9) | 1.9 | 1.6 | >50 |
| 615 | 6.1 | (3.4–10.7) | 2.5 | 3.2 | 50 |
| 616 | 24.0 | (15.6–36.8) | 1.0 | 1.4 | >50 |
| 617 | 54.9 | (42.9–70.4) | 1.1 | 1.1 | >50 |
| 618 | 24.0 | (9.6–59.5) | 1.2 | 1.1 | >50 |
| 619 | 44.6 | (32.0–62.3) | 1.0 | 1.0 | >50 |
| 620 | 41.3 | (32.9–51.7) | 1.6 | 1.1 | >50 |
| 621 | 36.9 | (22.6–60.3) | 1.8 | 1.5 | >60 |
| 622 | 21.0 | (16.1–27.5) | 1.1 | 1.7 | 50 |
| 623 | 13.1 | (9.9–17.2) | 1.4 | 1.8 | >30 |
| 624 | 47.2 | (41.3–53.2) | 0.9 | 1.0 | 100 |

TABLE 8-continued

| MRZ2/ | MES ED$_{50}$ mg/kg i.p. | | TI Tract | TI Rot. | Min Lethality mg/kg i.p. |
|---|---|---|---|---|---|
| 625 | 129.8 | (42.5–395.6) | 0.5 | 1.2 | >70 |
| 626 | 41.2 | (29.9–56.7) | 1.1 | 1.0 | >50 |
| 627 | 43.9 | (30.3–63.7) | 0.8 | 1.0 | 60 |
| 628 | 73.2 | (33.6–159.4) | 0.8 | 1.6 | >60 |
| 629 | 58.5 | (38.3–89.2) | 0.9 | 0.9 | 100 |
| 630 | >30 | | nc | nc | >30 |
| 631 | 30 | | nc | nc | >30 |
| 632 | 11.04 | (7.7–15.8) | 2.7 | 3.4 | >30 |
| 633 | 8.78 | (3.6–21.4) | 2.4 | 3.0 | 108 |
| 634 | >30 | | nc | nc | >30 |
| 635 | 31.59 | (21.3–46.8) | 1.3 | 1.4 | >50 |
| 639 | 5.87 | (3.8–9.0) | 2.6 | 4.4 | 30 |
| 640 | 8.18 | (5.7–11.8) | 2.3 | 3.3 | 108 |
| 641 | >50 | | nc | nc | >50 |
| 642 | 8.04 | (5.1–12.7) | 4.1 | 5.3 | |
| 643 | 18.65 | (10.8–32.2) | 1.3 | 2.4 | >50 |
| 644 | 52.98 | (27.8–100.8) | 0.5 | 0.6 | >35 |
| 645 | 65.61 | (43.8–98.2) | 0.6 | 0.6 | |
| 662 | 30.47 | (18.0–51.6) | 1.0 | 1.2 | >40 |
| 680 | 34.5 | (27.1–44.0) | 0.7 | 1.1 | >50 |
| 681 | 27.9 | (18.2–42.6) | 2.1 | 5.3 | >50 |
| 682 | 7.6 | (4.5–13.0) | 2.7 | 3.6 | >50 |
| 683 | 12.2 | (6.3–23.5) | 2.7 | 3.5 | >50 |
| 705 | 9.55 | (4.3–21.1) | 3.9 | 5.4 | >50 |
| Memantine | 6.9 | (5.4–8.8) | 2.9 | 2.5 | >108 |
| Amantadine | 184.0 | (122–279) | 0.5 | 0.6 | >324 |
| MK-801 | 0.16 | (0.13–0.21) | 1.0 | 1.2 | >108 |

Table 8

Effect of the present amino-alkyl-cyclohexane derivatives and standard uncompetitive NMDA receptor antagonists on convulsions induced by maximal electroshock (MES). Values are ED$_{50}$S in mg/kg (95% confidence limits are shown in parentheses). The therapeutic index (TI) was also calculated as the ED$_{50}$ for inhibition of traction reflex (Tract.) impairment or rotarod failure (Rot.) divided by the ED$_{50}$ for MES-induced seizure-induced convulsions. Most of the amino-alkyl-cyclohexane derivatives showed no acute toxicity, i.e., minimal lethal doses were above 50 mg/kg.

TABLE 9

| MRZ | MK-801 Ki ($\mu$M) | SEM | Patch Clamp IC$_{50}$($\mu$M) | SEM | Glut Tox IC$_{50}$ ($\mu$M) | SEM |
|---|---|---|---|---|---|---|
| 557 | 19.92 | 2.98 | 18.50 | 2.70 | 6.70 | 2.00 |
| 579 | 1.47 | 0.13 | 1.29 | 0.20 | 2.16 | 0.03 |
| 580 | 17.84 | 1.33 | 12.90 | 0.40 | 5.60 | 0.80 |
| 600 | 2.28 | 0.21 | 3.49 | 0.47 | 2.10 | 0.20 |
| 601 | 8.09 | 0.43 | 10.00 | 0.20 | 3.50 | 0.30 |
| 607 | 7.74 | 0.29 | 13.90 | 1.50 | 10.10 | 2.20 |
| 614 | 13.59 | 0.12 | 13.90 | 1.90 | 1.26 | 0.19 |
| 615 | 2.42 | 0.11 | 2.90 | 0.40 | 2.29 | 0.15 |
| 616 | 10.42 | 2.00 | 33.20 | 2.50 | 9.10 | 2.10 |
| 617 | 38.03 | 8.56 | 63.90 | 7.70 | >70 | nc |
| 618 | 24.02 | 5.33 | 57.50 | 11.90 | 17.60 | 2.90 |
| 619 | 57.76 | 8.96 | 60.90 | 5.40 | 30.90 | 2.90 |
| 620 | 25.48 | 4.34 | 99.00 | 10.40 | 38.40 | 1.60 |
| 621 | 32.20 | 8.30 | 92.40 | 19.50 | >100 | nc |
| 622 | 13.32 | 3.29 | 58.20 | 8.50 | 19.30 | 8.10 |
| 623 | 3.16 | 0.31 | 3.70 | 0.70 | 4.50 | 0.60 |
| 624 | 15.14 | 2.36 | 31.00 | 3.60 | 2.70 | 0.60 |
| 625 | 52.61 | 3.69 | 244.90 | 40.50 | 39.40 | 6.30 |
| 626 | 16.48 | 4.21 | 9.60 | 2.00 | 19.00 | 3.33 |
| 627 | 70.95 | 11.22 | 150.00 | 27.00 | 26.60 | 5.70 |
| 628 | 49.18 | 4.35 | 125.50 | 22.60 | 27.30 | 4.50 |
| 629 | 49.28 | 2.60 | 218.60 | 39.30 | >300 | nc |
| 630 | 49.10 | 5.09 | 100.00 | 11.00 | >100 | nc |
| 631 | 65.29 | 13.64 | >100 | nc | >100 | nc |
| 632 | 2.88 | 0.28 | 6.40 | 0.60 | 11.20 | 0.27 |
| 633 | 5.18 | 1.11 | 13.90 | 3.20 | 6.10 | 1.84 |
| 634 | 13.40 | 4.25 | 10.80 | 2.70 | 19.00 | 3.50 |
| 635 | 15.01 | 1.85 | 21.00 | 4.70 | 8.18 | 1.43 |
| 639 | 4.17 | 0.32 | 7.40 | 1.00 | 6.33 | 0.16 |
| 640 | 4.83 | 0.56 | 14.60 | 1.90 | 8.35 | 0.51 |
| 641 | 143.33 | 36.76 | >100 | nc | >100 | nc |
| 642 | 12.72 | 3.15 | 42.50 | 6.50 | 29.30 | 3.34 |

TABLE 9-continued

| MRZ | MK-801 Ki ($\mu$M) | SEM | Patch Clamp IC$_{50}$($\mu$M) | SEM | Glut Tox IC$_{50}$ ($\mu$M) | SEM |
|---|---|---|---|---|---|---|
| 643 | 4.66 | 0.12 | 13.50 | 1.70 | 12.00 | 0.87 |
| 644 | 4.84 | 0.35 | 4.10 | 1.80 | 4.30 | 0.42 |
| 645 | 60.17 | 8.38 | 20.40 | 3.60 | >100 | nc |
| 662 | 3.44 | 0.77 | 1.50 | 0.05 | 0.53 | 0.04 |
| 680 | 29.96 | 8.96 | 43.00 | 5.5 | 35.6 | 4.1 |
| 681 | 19.21 | 4.81 | 30.00 | 3.4 | 26.9 | 3.1 |
| 682 | 1.99 | 0.19 | 3.90 | 0.56 | 3.11 | 0.20 |
| 683 | 4.44 | | 4.30 | 0.70 | 5.08 | 0.34 |
| 705 | 7.14 | 1.7 | 25.40 | 4.1 | nt | nt |
| Amantadine | 25.87 | 2.99 | 80.80 | 10.40 | 36.91 | 5.52 |
| Memantine | 2.45 | 0.91 | 2.87 | 0.44 | 1.40 | 0.10 |
| MK-801 | 6.56 * 10$^{-3}$ | 0.33 * 10$^{-3}$ | 0.1400 | 0.1000 | 0.0130 | 0.0020 |

Table 9

Effect of amino-alkyl-cyclohexane derivatives and standard uncompetitive NMDA receptor antagonists on [$^3$H]-(+)-MK-801 binding, NMDA-induced currents in patch clamp experiments, and glutamate toxicity in cultured cortical neurones. Binding Ki values are means ±SEM of 3–5 experiments and were determined according to the Cheng-Prusoff relationship with a Kd for MK-801 of 4.6 nM. IC$_{50}$s (±SEM) in patch clamp and glutamate toxicity experiments were determined from data from at least 3 concentrations producing between 15 and 85% inhibition and at least 5 cells/well per concentration.

Figure 1:
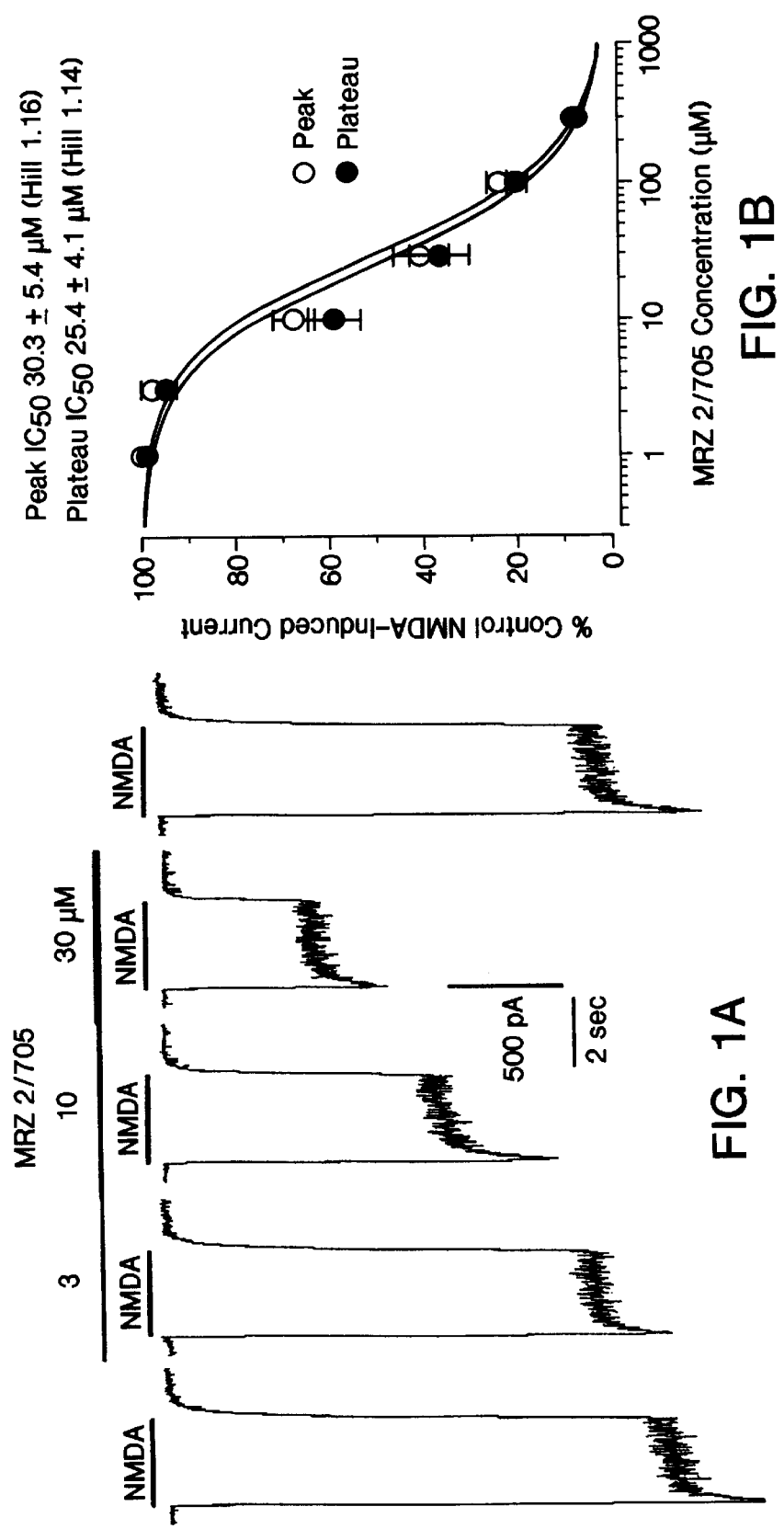
FIG. 1A and FIG. 1B show values obtained for these effects using MRZ 2/705.
Figure 2:
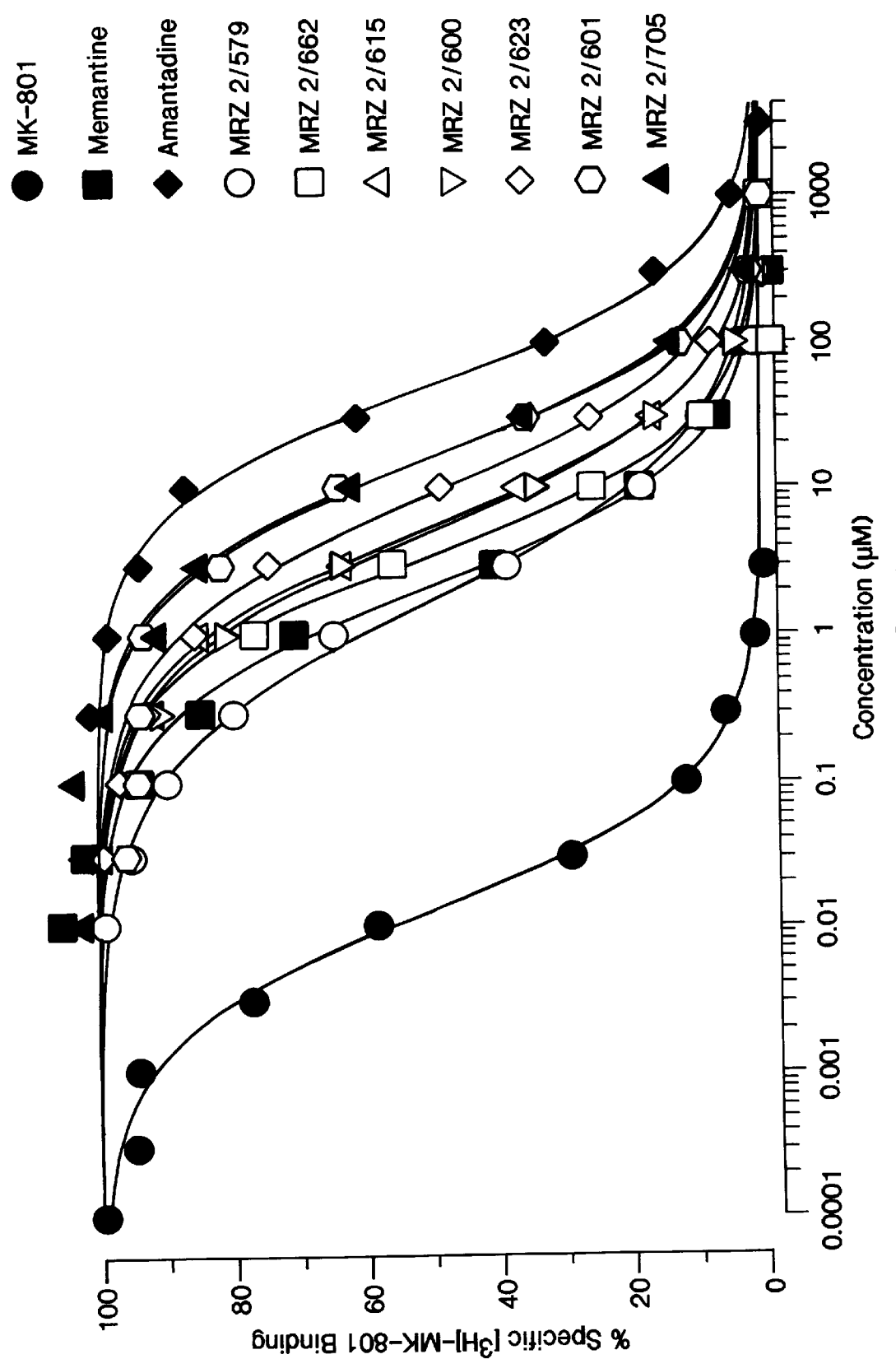
FIG. 2 shows the values obtained for various compounds of the invention and reference standards in the specific [$^3$H]-MK-801 binding test plotted against concentration.

Further research with respect to MRZ 2/616, 1-amino-1,3,5-trimethylcyclohexane, showed it to be a 1:2 mixture of the isomers 1,cis-3,cis-5-trimethyl- and 1,trans-3,trans-5-trimethylcyclohexylamine, which was separated in conventional manner into the individual pure enantiomeric forms MRZ 2/680, the 1-amino-1(trans),3(trans),5-trimethylcyclohexane and MRZ 2/681, 1-amino-1(cis),3(cis),5-trimethylcyclohexane as the hydrochloride and hydrochloride hydrate, respectively.

In addition, MRZ 2/632 and MRZ 2/633 were separated in conventional manner into their pure enantiomeric forms, MRZ 2/682 and MRZ 2/683, respectively 1-amino-(1R,5S) trans-3-ethyl-1,5,5-trimethylcyclohexane as the hydrochloride and 1-amino-(1S,5S)cis-3-ethyl-1,5,5-trimethylcyclohexane as the hydrochloride hydrate. All of these compounds, and their pure enantiomers, MRZ 2/616, MRZ 2/680, MRZ 2/681, MRZ 2/682 and MRZ 2/683, appear in the foregoing Tables along with the pharmacological data relating thereto.

The analytical certificates for these five (5) MRZ compounds follow:

MRZ 2/616

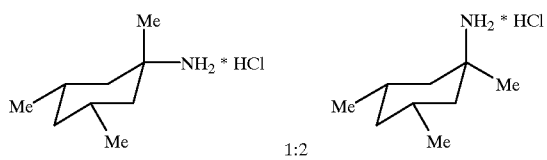

1,cis-3,cis-5-Trimethyl- and 1,trans-3,trans-5-trimethylcyclohexylamines hydrochlorides (–1:2)

Molecular formula: C$_9$H$_{19}$N*HCl Molecular weight: 177.7 Melting point: 280–282° C. PMR spectrum: (CDCl$_3$, TMS) δ: 0.90 (6H, d, 5.5 Hz, 3,5-CH$_3$); 1.0–1.3 (2H, m, 4-CH$_2$); 1.44 and 1.50 (3 H, both s, 1-CH$_3$); 1.55–2.4 (6H, m, 2-CH$_2$, 6-CH$_2$, 3-CH and 5-CH) and 8.25 ppm (3H, br s, NH$_3^+$). Solubility: soluble in water, chloroform. Elemental analysis: Found (%) C, 60.7; H, 11.5; N, 7.7. Calculated (%) C, 60.8; H, 11.3; N, 7.9. Impurities: less than 2.5% (for free amine: GC, MN-OV-1 (Fused Silica), 25 m*0.53 mm, d$_f$=1.0 μ, 50–270° C. (10° C./min)).

MRZ 2/680

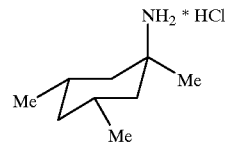

1,trans-3,trans-5-Trimethylcyclohexylamine Hydrochloride

Molecular formula: C$_9$H$_{19}$N*HCl Molecular weight: 177.7 Melting point: >280° C. PMR spectrum: (CDCl$_3$, TMS) δ: 0.89 (6H, d, J=6 Hz, 3,5-CH$_3$); 0.9–2.3 (8H$_1$, m, ring protons); 1.44 (3H, s, 1-CH$_3$) and 8.25 ppm (3H, br s, NH$_3^+$). Solubility: soluble in water, chloroform. Elemental analysis: Found (%) C, 60.7; H, 11.7; N, 7.7. Calculated (%) C, 60.8; H, 11.3; N, 7.9. Impurities: 2% (for free amine: GC, MN-OV-1 (Fused Silica), 25 m*0.53 mm, d$_f$=1.0 μ, 50–270° C. (10° C./min)).

MRZ 2/681

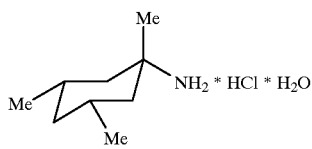

1,cis-3,cis-5-Trimethylcyclohexylamine hydrochloride Hydrate

Molecular formula; $C_9H_{19}N*HCl*H_2O$ Molecular weight: 195.7 Melting point; 237–238° C. PMR spectrum: (CDCl$_3$, TMS) δ: 0.89 (6H, d, J=5.5 Hz, 3,5-CH$_3$); 0.9–2.3 (8H, m, ring protons); 1.47 (3H, s, 1-CH$_3$) and 8.3 ppm (3H, br s, NH$_3^+$). Solubility: soluble in water, chloroform. Elemental analysis: Found (%) C, 55.3; H, 11.6; N, 7.1. Calculated (%) C, 55.2; H, 11.3; N, 7.2. Impurities: 1.5% (for free amine: GC, MN-OV-1 (Fused Silica), 25 m*0.53 mm, d$_f$=1.0 μ, 50–270° C. (10° C/min)).

MRZ 2/682

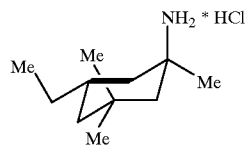

(1R, 5S) trans-3-Ethyl-1,5,5-trimethylcyclohexylamine Hydrochloride

Molecular formula; $C_{11}H_{23}N*HCl$ Molecular weight: 205.8 Melting point: >280° C. (subl.) PMR spectrum: (CDCl$_3$, TMS) δ: 0.8–1.0 (m) and 0.91 (s, total 6H, 5-CH$_{3eq}$ and CH$_3$-ethyl); 1.22 (3H, s ,5-CH$_{3ax}$); 1.44 (3H, s, 1-CH$_3$); 1.0–2.3 (9H, m, ring protons and CH$_2$-ethyl) and 8.2 ppm (3H, br s, NH$_3^+$). Solubility; soluble in chloroform, poor soluble in water. Elemental analysis: Found (%) C, 64.2; H, 11.9, N, 6.6. Calculated (%) C, 64.2; H, 11.8; N, 6.8. Impurities: less than 1% (for free amine: GC, MN-OV-1 (Fused Silica), 25 m*0.53 mm, d$_f$=1.0 μ, 50–270° C. (10° C/min)).

M MRZ 2/683

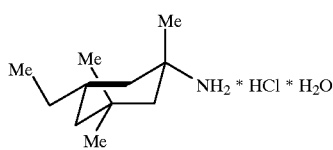

(1S, 5S) cis-3-Ethyl-1,5,5-trimethylcyclohexylamine Hydrochloride Hydrate

Molecular formula: $C_{11}H_{23}N*HCl*H_2O$ Molecular weight: 223.8 Melting point: 243–245° C. PMR spectrum: (CDCl$_3$, TMS) δ: 0.88 (m) and 0.96 (s, total 9H, 5-CH$_3$ and CH$_3$-ethyl); 1.50 (3H, s, 1-CH$_3$); 1.0–2.15 (9H, m, ring protons and CH$_2$-ethyl) and 8.35 ppm (3H, br s, NH$_3^+$). Solubility: soluble in chloroform, poor soluble in water. Elemental analysis: Found (%) C, 59.9; H, 11.8; N, 6.2. Calculated (%) C, 59.0; H, 11.6, N, 6.3. Impurities: less than 1% (for free amine: GC, MN-OV-1 (Fused Silica), 25 m*0.53 mm, d$_f$=1.0 μ, 50–270° C. (10° C/min)).

In conclusion, from the foregoing, it is apparent that the present invention provides novel, valuable, and unpredictable applications and uses of the compounds of the present invention, which compounds comprise the active principle according to the present invention, as well as novel pharmaceutical compositions thereof and methods of preparation thereof and of treating therewith, all possessed of the foregoing more specifically-enumerated characteristics and advantages.

The high order of activity of the active agent of the present invention and compositions thereof, as evidenced by the tests reported, is indicative of utility based on its valuable activity in human beings as well as in lower animals. Clinical evaluation in human beings has not been completed, however. It will be clearly understood that the distribution and marketing of any compound or composition falling within the scope of the present invention for use in human beings will of course have to be predicated upon prior approval by governmental agencies, such as the U.S. Federal Food and Drug administration, which are responsible for and authorized to pass judgment on such questions.

Conclusions

The present 1-amino-alkylcyclohexanes represent a novel class of systemically-active, uncompetitive NMDA receptor antagonists with rapid blocking/unblocking kinetics and strong voltage-dependency. In view of their relatively low potency and associated rapid kinetics, they will be useful therapeutics in a wide range of CNS disorders which involve disturbances of glutamatergic transmission.

These compounds accordingly find application in the treatment of the following disorders of a living animal body, especially a human. 1. Acute excitotoxicity such as ischaemia during stroke, trauma, hypoxia, hypoglycemia, and hepatic encephalopathy. 2. Chronic neurodegenerative diseases such as Alzheimer's disease, vascular dementia, Parkinson's disease, Huntington's disease, multiple sclerosis, amyotrophic lateral sclerosis, AIDS-neurodegeneration, olivopontocerebellar atrophy, Tourette's syndrome, motor neurone disease, mitochondrial dysfunction, Korsakoff syndrome, Creutzfeldt-Jakob disease. 3. Other disorders related to long term plastic changes in the central nervous system such as chronic pain, drug tolerance, dependence and addiction (e.g., opioids, cocaine, benzodiazepines, and alcohol). 4. Epilepsy, tardive dyskinesia, schizophrenia, anxiety, depression, acute pain, spasticity, and tinnitus. 5. In addition, as already stated, due at least in part to their amine substituent, the compounds of the present invention are also effective in non-NMDA indications, exhibiting immunomodulatory activity, antimalaria potency, anti-Borna virus activity, and anti-Hepatitis C activity.

It is to be understood that the invention is not to be limited to the exact details of operation, or to the exact compositions, methods, procedures, or embodiments shown and described, as obvious modifications and equivalents will be e apparent to one skilled in the art, and the invention is therefore to be limited only by the full scope which can be legally accorded to the appended claims.

REFERENCES

1. R. L. Frank, H. K. Hall (1950) J. Am. Chem. Soc. 72:1645–1648.
2. G. A. Hiegel, P. Burk. (1973) J. Org. Chem. 38:3637–3639.
3. N. F. Firrell, P. W. Hickmott. (1970) J. Chem. Soc. C:716–719.

4. G. H. Posner, L. L. Frye. (1984) Isr. J. Chem. 24:88–92.
5. G. L. Lemiere, T. A. van Osselaer, F. C. Anderweireldt. (1978) Bull. Soc. Chim. Belg. 87:771–782.
6. H. O. House, J. M. Wilkins. (1976) J. Org. Chem. 41:(25) 4031–4033.
7. A. R. Greenaway, W. B. Whalley. (1976) J. Chem. Soc. P. T. 1.:1385–1389.
8. S. Matsuzawa, Y. Horiguchi, E. Nakamura, I. Kuwajima. (1989) Tetrahedron 45:(2) 349–362.
9. H. O. House, W. F. Fischer. (1968) J. Org. Chem. 33:(3) 949–956.
10. Chiurdoglu, G., Maquestiau, A. (1954) Bull. Soc. Chim. Belg. 63: 357–378.
11. Zaidlewicz, M., Uzarewicz A., Zacharewicz, W. (1964) Roczniki Chem. 38: 591–597.
12. Crossley, A. W., Gilling, C. (1910) J. Chem. Soc. 2218.
13. Zaidlewicz, M., Uzarewicz, A. (1971) Roczniki Chem. 45: 1187–1194.
14. Lutz, E. T., van der Maas, J. H. (1981) Spectrochim. Acta, A. 38A: 283.
15. Lutz, E. T., van der Maas, J. H. (1981) Spectrochim. Acta, A. 37A: 129–134.
16. Ramalingam K., Balasubramanian, M., Baliah, V. (1972) Indian J. Chem. 10: 366–369.
17. Hamlin, K. E., Freifelder, M. (1953) J. Am. Chem. Soc. 75: 369–373.
18. Hassner, A., Fibinger, R., Andisik, D. (1984) J. Org. Chem. 49: 4237–4244.
19. W. Danysz, C. G. Parsons, I. Bresink, G. Quack (1995) Drug News Perspect. 8:261–277.
20. J. D. Leander, R. R. Lawson, P. L., Ornstein, D. M. Zimmerman (1988) Brain Res. 448:115–120.
21. C. G. Parsons, G. Quack, I. Bresink, L. Baran, E. Przegalinski, W. Kostowski, P. Krzascik, S. Hartmann, W. Danysz (1995). Neuropharmacology 34:1239–1258.
22. M. A. Rogawski (1993) Trends Pharmacol. Sci. 14:325–331.
23. Booher J. and Sensenbrenner M. (1972). Neurobiology 2:97–105.
24. Dichter, M. (1987) Brain Research 149:279.

We claim:

1. A method-of-treating a living animal for alleviation of a condition which is alleviated by an NMDA receptor antagonist, or for its immunomodulatory, antimalarial, anti-Borna virus, or anti-Hepatitis C effect, comprising the step of administering to the said living animal an amount of a 1-aminoalkylcyclohexane compound selected from the group consisting of those of the formula

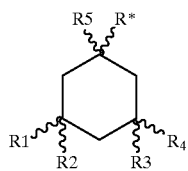

wherein R* is —$(CH_2)_n$, $(CR^6R^7)_m$—$NR^8R^9$
wherein n+m=0, 1, or 2
wherein $R^1$ through $R^7$ are independently selected from the group consisting of hydrogen and lower-alkyl (1–6C), wherein $R^8$ and $R^9$ are independently selected from the group consisting of hydrogen and lower-alkyl (1–6C) or together represent lower-alkylene —$(CH_2)_x$— wherein x is 2 to 5, inclusive, and optical isomers, enantiomers, hydrates, and pharmaceutically-acceptable salts thereof, which is effective for the said purpose.

2. A method of claim 1 wherein $R^1$ through $R^5$ are methyl.
3. A method of claim 1 wherein $R^1$ is ethyl.
4. A method of claim 1 wherein $R^2$ is ethyl.
5. A method of claim 1 wherein $R^3$ is ethyl.
6. A method of claim 1 wherein $R^4$ is ethyl.
7. A method of claim 1 wherein $R^5$ is ethyl.
8. A method of claim 1 wherein $R^5$ is propyl.
9. A method of claim 1 wherein $R^6$ or $R^7$ is methyl.
10. A method of claim 1 wherein $R^6$ or $R^7$ is ethyl.
11. A method of claim 1 wherein the compound is selected from the group consisting of
1-amino-1,3,5-trimethylcyclohexane,
1-amino-1(trans),3(trans),5-trimethylcyclohexane,
1-amino-1(cis),3(cis),5-trimethylcyclohexane,
1-amino-1,3,3,5-tetramethylcyclohexane,
1-amino-1,3,3,5,5-pentamethylcyclohexane,
1-amino-1,3,5,5-tetramethyl-3-ethylcyclohexane,
1-amino-1,5,5-trimethyl-3,3-diethylcyclohexane,
1-amino-1,5,5-trimethyl-cis-3-ethylcyclohexane,
1-amino-(1S,5S)cis-3-ethyl-1,5,5-trimethylcyclohexane,
1-amino-1,5,5-trimethyl-trans-3-ethylcyclohexane,
1-amino-(1R,5S)trans-3-ethyl-1,5,5-trimethylcyclohexane,
1-amino-1-ethyl-3,3,5,5-tetramethylcyclohexane,
1-amino-1-propyl-3,3,5,5-tetramethylcyclohexane,
N-methyl-1-amino-1,3,3,5,5-pentamethylcyclohexane,
N-ethyl-1-amino-1,3,3,5,5-pentamethylcyclohexane, and
N-(1,3,3,5,5-pentamethylcyclohexyl) pyrrolidine, and optical isomers, enantiomers, hydrates and pharmaceutically-acceptable salts of any of the foregoing.

12. A method of claim 1 wherein the compound is administered in the form of a pharmaceutical composition thereof comprising the compound in combination with one or more pharmaceutically-acceptable diluents, excipients, or carriers.

* * * * *

UNITED STATES PATENT AND TRADEMARK OFFICE
CERTIFICATE OF CORRECTION

PATENT NO. : 6,071,966
DATED : April 25, 2000
INVENTOR(S) : M. Gold, W. Danysz, C.G.R. Parsons, I. Kalvinsh, V. Kauss, A. Jirgensons It is certified that error appears in the above-identified patent and that said Letters Patent is hereby corrected as shown below:

Column 5,
Line 12: Insert --METHODS-- as title.
Line 13: Insert --CHEMISTRY-- as subtitle.

Column 6,
Line 25(approx.): Example #11 and formula: should be over Example 12 and formula.
Line 40(approx): Example #10: at the upper right hand side, "OH" should be --$N_3$--.
Line 50(approx): Example #5, upper right hand corner: "$R^7$*HCl" should read --$R^9$*HCl--.
Line 50(approx): Replace "Example #12" (second instance) with --Example #13-- (as shown).

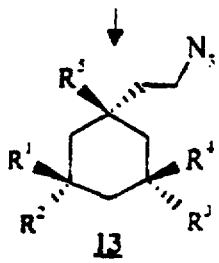

Column 7,
Line 33: [commerce" should read: --[commerc --.

Column 8,
Line 32: "($R^3$=R =)" should read: --($R^3$=$R^5$= --.

UNITED STATES PATENT AND TRADEMARK OFFICE
CERTIFICATE OF CORRECTION

PATENT NO.    : 6,071,966
DATED         : April 25, 2000
INVENTOR(S)   : M. Gold, W. Danysz, C.G.R. Parsons, I. Kalvinsh, V. Kauss, A. Jirgensons It is certified that error appears in the above-identified patent and that said Letters Patent is hereby corrected as shown below:

Column 11,
Line 3: "ana" should read: --and--.
Line 7: "223g" should read: --2.23g--
Line 42: "(2H,s,4 - CH?); " should read: -- (2H,s,4 - $CH_2$); --.
Line 53: "-15C." should read: --15°C.--.

Column 13,
Line 12(approx) Table 2: Under column "Yield", "96" should read -- 88 --.
Line 11(approx) Table 3: Under column "Yield" "60" should read -- 65 --.
Line 13(approx) Table 3: Under column $^1$H-NMR($CDCl_3$, TMS) & ppm, "9.9-2.0: should read -- 0.9-2.0 --.
Line 17(approx) Table 3: Under column $^1$H-NMR($CDCl_3$, TMS) & ppm, "9.95-1.9 (7H,m)" should read: -- 0.95-1.9 (7H,m) --.
Line 20(approx) Table 3: Under column $^1$H-NMR($CDCl_3$, TMS) & ppm, "1.95 (9Hm)" should read: -- 0.95 (9H,m) --.

Columns 15 & 16,
Line 8(approx) Table 3: "1.16 (6H,s);" should read: -- 1.18(6H,s); --.
Line 10(approx) Table 4: at the beginning of line "626" should read: --628 --.
Line 34(approx) Table 4: line beginning with "645", "$C_{13}$" should read --$C_{14}$ --.
Line 39(approx) Table 4: line beginning with "641", "89" at the end of the line should read -- 69 --.
Last line of Table 5: Delete 2nd instance: "1.50 (34H,s);".

Column 17,
Line 15(approx), Table 5: "10-2.2(11H,m);" should read: -- 1.0-2.2(11H,m); --.
Line 17(approx), Table 5: "196 (2H,q,7Hz);" should read: -- 1.96(2H,q,7Hz); --.
Line 18(approx) Table 5: "135-2.0(4H,m);" should read: -- 1.35-2.00(4H,m); --.
Line 30(approx) Table 5: "3.41(1H,m);" should read: -- 3.47(1H,m); --.

Column 25,
Line 41: "glycine," should read: -- $glycine_B$ --.

UNITED STATES PATENT AND TRADEMARK OFFICE
CERTIFICATE OF CORRECTION

PATENT NO. : 6,071,966
DATED : April 25, 2000
INVENTOR(S) : M. Gold, W. Danysz, C.G.R. Parsons, I. Kalvinsh, V. Kauss, A. Jirgensons It is certified that error appears in the above-identified patent and that said Letters Patent is hereby corrected as shown below:

Columns 27&28,
Line 6(approx): Row starting with number 580, "0.6" should read -- 0.8 --.
Line 7(approx): Row starting with number 600, "24" should read -- 2.4 --.
Line 9(approx): Row starting with number 607, "13.6" should read: -- 13.8 --.
Line 12(approx): Row starting with 616, "150" should read -- 15.0 --.
Line 18(approx): Row starting with 622, "150" should read -- 15.0 --.
Line 26(approx): Row starting with 630, "443" should read -- 44.3 --.
Line 29(approx): Row starting with 633, "6.6" should read: -- 6.8 --.
Line 31(approx): Row starting with 635, at the end of the line, "21.3-46.6" should read -- 21.3-46.8 --.
Line 32(approx): Row starting with 639, at the end of the line, "3.6-9.0" should read: --3.8-9.0 --.
Line 36(approx): row starting with 643, "16.65" should read -- 18.65 --.

Column 29,
Line 6: "TSEM" should read -- (+SEM) --.
Line 14: Delete the " - " before the word "also:.
Line 32: "(2-06g," should read -- (2.06g, --.
Line 34: At the end of the line, "the" should read: -- then --.
Line 43: At the end of the line, "3,5-H$_3$);" should read -- 3,5 - CH$_3$); --.

Column 30,
Line 8 of Table 8 (#615): At the end of the line, "50" should read: -- >50 --.
Line 10: At the end of the line, "vas" should read -- was --.
Line 13(approx) of Table 8 (#620): "1.1" should read -- 1.5 --.
Line 17(approx) of Table 8 (last line): "(41.3-53.2)" should read -- (41.8-53.2) --.

UNITED STATES PATENT AND TRADEMARK OFFICE
CERTIFICATE OF CORRECTION

PATENT NO. : 6,071,966
DATED : April 25, 2000
INVENTOR(S) : M. Gold, W. Danysz, C.G.R. Parsons, I. Kalvinsh, V. Kauss, A. Jirgensons It is certified that error appears in the above-identified patent and that said Letters Patent is hereby corrected as shown below:

Column 31,
Line 21(approx) of Table 8 (#681): "5.3" should read -- 5.8 --.

Column 32,
Line 6 of Table 9 (#607): "13.90" should read: -- 13.80 --.

Column 34,
Line 61: "8H$_1$,m," should read: -- (8H,m, --.

Column 35,
Line 47: "M MRZ 2/683" should read: -- MRZ 2/683 --.

Column 36,
Line 57: "be e apparent: should read: -- be apparent --.

Signed and Sealed this

Fourteenth Day of August, 2001

*Attest:*

NICHOLAS P. GODICI
*Attesting Officer* *Acting Director of the United States Patent and Trademark Office*